(12) United States Patent
Bourelle et al.

(10) Patent No.: US 12,102,599 B2
(45) Date of Patent: Oct. 1, 2024

(54) PRESSURIZED GAS POWERED LIQUID TRANSFER DEVICE AND SYSTEM

(71) Applicant: ENABLE INJECTIONS, INC., Cincinnati, OH (US)

(72) Inventors: Dylan L. Bourelle, Cincinnati, OH (US); Daniel Geiger, Newport, KY (US); Matthew J. Huddleston, Loveland, OH (US); James Lowe, Cincinnati, OH (US); Joetta Renee Palmer, Mason, OH (US); David Stefanchik, Morrow, OH (US)

(73) Assignee: Enable Injections, Inc., Cincinnati, OH (US)

( * ) Notice: Subject to any disclaimer, the term of this patent is extended or adjusted under 35 U.S.C. 154(b) by 0 days.

(21) Appl. No.: 18/163,954

(22) Filed: Feb. 3, 2023

(65) Prior Publication Data

US 2023/0190582 A1  Jun. 22, 2023

Related U.S. Application Data

(63) Continuation of application No. 16/755,786, filed as application No. PCT/US2018/056130 on Oct. 16, 2018, now Pat. No. 11,571,361.

(60) Provisional application No. 62/572,911, filed on Oct. 16, 2017.

(51) Int. Cl.
*A61J 1/20* (2006.01)

(52) U.S. Cl.
CPC .............. *A61J 1/2096* (2013.01); *A61J 1/201* (2015.05); *A61J 1/2072* (2015.05)

(58) Field of Classification Search
CPC .......... A61J 1/2072; A61J 1/201; A61J 1/2096
See application file for complete search history.

(56) References Cited

U.S. PATENT DOCUMENTS

| 5,329,976 A * | 7/1994 | Haber ................... A61J 1/2096 604/407 |
| 2008/0208114 A1 * | 8/2008 | Landau ................... A61M 5/30 604/68 |
| 2011/0220116 A1 | 9/2011 | Lowenstein et al. |

(Continued)

FOREIGN PATENT DOCUMENTS

| JP | H 8-38532 A | 2/1996 |
| WO | WO2016/154413 A1 | 9/2016 |

OTHER PUBLICATIONS

Notice of Reasons for Refusal and English-language machine translation, counterpart Japanese App. No. 2022-148009 (Jun. 6, 2023) (8 pages).

*Primary Examiner* — Jason K Niesz
(74) *Attorney, Agent, or Firm* — Cook Alex Ltd.

(57) ABSTRACT

A transfer device for transferring a medical fluid from a vial to a medical fluid injection device includes a vial holder where a vial spike positioned within the vial holder is configured to enter a vial containing a medical fluid when the vial is inserted into the vial holder. An expansion chamber having an interior cavity is in fluid communication with the vial spike. A pressurized gas cartridge is positioned with the interior cavity of the expansion chamber, while a puncture tip is configured to puncture the pressurized gas cartridge when actuated by a user. The vial spike is also configured to be in fluid communication with an injection device attached to the transfer device.

20 Claims, 25 Drawing Sheets

(56) References Cited

U.S. PATENT DOCUMENTS

2017/0196771 A1\* 7/2017 Hooven ................ G16H 40/67
2018/0110922 A1\* 4/2018 Dunki-Jacobs ....... A61M 5/152

\* cited by examiner

PRESSURIZED GAS POWERED LIQUID TRANSFER DEVICE AND SYSTEM

CLAIM OF PRIORITY

This application is a Continuation of U.S. application Ser. No. 16/755,786, filed Apr. 13, 2020, which is the U.S. National Stage of PCT International Patent Application No. PCT/US2018/056130, filed Oct. 16, 2018, which claims priority to and the benefit of U.S. Provisional Patent Application No. 62/572,911, filed Oct. 16, 2017, the contents of each of which are hereby incorporated by reference in their entirety.

FIELD OF THE INVENTION

The present subject matter relates generally to devices for transferring a fluid from a vial to a medical device and, in particular, to a pressurized gas powered device and system for transferring liquid medication from a source vial to an injection device and/or for mixing, diluting or reconstituting a medication and transferring the resulting liquid medication into an injection device.

BACKGROUND

Injection devices that are worn by a patient temporarily or for extended periods are well known in the medical field. The subject matter of this application relates to a transfer device for use particularly but not exclusively with the injection device described in commonly assigned PCT Published Application No. WO 2014/204894, published Dec. 24, 2014, and which is hereby incorporated by reference in its entirety. That injection device includes an internal resilient bladder that may be filled with any suitable injectable medicament, whether drug, antibiotic, biologic or other injectable, for subcutaneous injection, typically a bolus injection, into a patient while the device is being worn by the patient.

This injection device must be filled (wholly or partially) with the desired injectable before injection into the patient. The above PCT published application also discloses a variety of transfer devices for transferring an injectable into the injection device from a source such as a vial or vials. In some situations, the injectable must be diluted or reconstituted, and various devices are disclosed in the above application for accomplishing that. The present application discloses additional novel designs and improvements, allowing lower cost of manufacture and less waste to dispose, for such transfer devices for transferring, diluting and/or reconstituting. The transfer devices described herein may be variously referred to as transfer module, accessories, add-ons or by other suitable terminology, without intending any limitation on the structure or function of the device not set forth herein.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a transfer device for transferring a medical fluid from a vial to a medical fluid injection device includes a vial elevator configured to receive a vial containing a medical fluid and a vial elevator shaft within which the vial elevator moves between an extended position and a retracted position. A vial spike is positioned within the vial elevator shaft so that the vial spike is positioned within the vial when the vial elevator is in the retracted position. An expansion chamber has an interior cavity and a pressurized gas cartridge is positioned with the interior cavity of the expansion chamber. A puncture tip is configured to puncture the pressurized gas cartridge when actuated by a user. The vial spike is in fluid communication with the interior cavity of the expansion chamber and is configured to be in fluid communication with an injection device attached to the transfer device and a vial positioned within the vial elevator when the vial elevator is in the retracted position and the vial spike is positioned in the vial.

In another aspect, A transfer device for transferring a medical fluid from a vial to a medical fluid injection device includes a vial holder with a vial spike positioned within the vial holder and configured to enter a vial containing a medical fluid when the vial is inserted into the vial holder. An expansion chamber has an interior cavity in fluid communication with the vial spike and a pressure relief bore. A pressurized gas cartridge positioned with the interior cavity of the expansion chamber. A puncture tip is configured to puncture the pressurized gas cartridge when actuated by a user. The vial spike is configured to be in fluid communication with an injection device attached to the transfer device. A plunger rod is slidably positioned within the pressure relief bore and configured to move between a closed position and a venting position.

In still another aspect, a transfer device for transferring a medical fluid from a vial to a medical fluid injection device includes a vial holder with a vial spike positioned within the vial holder and configured to enter a vial containing a medical fluid when the vial is inserted into the vial holder. An expansion chamber has an interior cavity in fluid communication with the vial spike. A pressurized gas cartridge is positioned within the interior cavity of the expansion chamber. A puncture tip is configured to puncture the pressurized gas cartridge when actuated by a user. A vent filter includes a housing having a fluid inlet, a liquid outlet and a gas outlet, a hydrophilic membrane positioned in the housing and in fluid communication with the fluid inlet and the liquid outlet and a hydrophobic membrane positioned in the housing and in fluid communication with the fluid inlet and the gas outlet. The vial spike is configured to provide medical fluid from a vial inserted in the vial holder to the fluid inlet of the vent filter so that a liquid portion of the medical fluid flows through the hydrophilic member and out of the housing through the liquid outlet. The liquid outlet is configured to be in fluid communication with an injection device attached to the transfer device. A gas portion of the medical fluid flows through the hydrophobic membrane and out of the housing through the gas outlet.

DESCRIPTION

Figure 1:
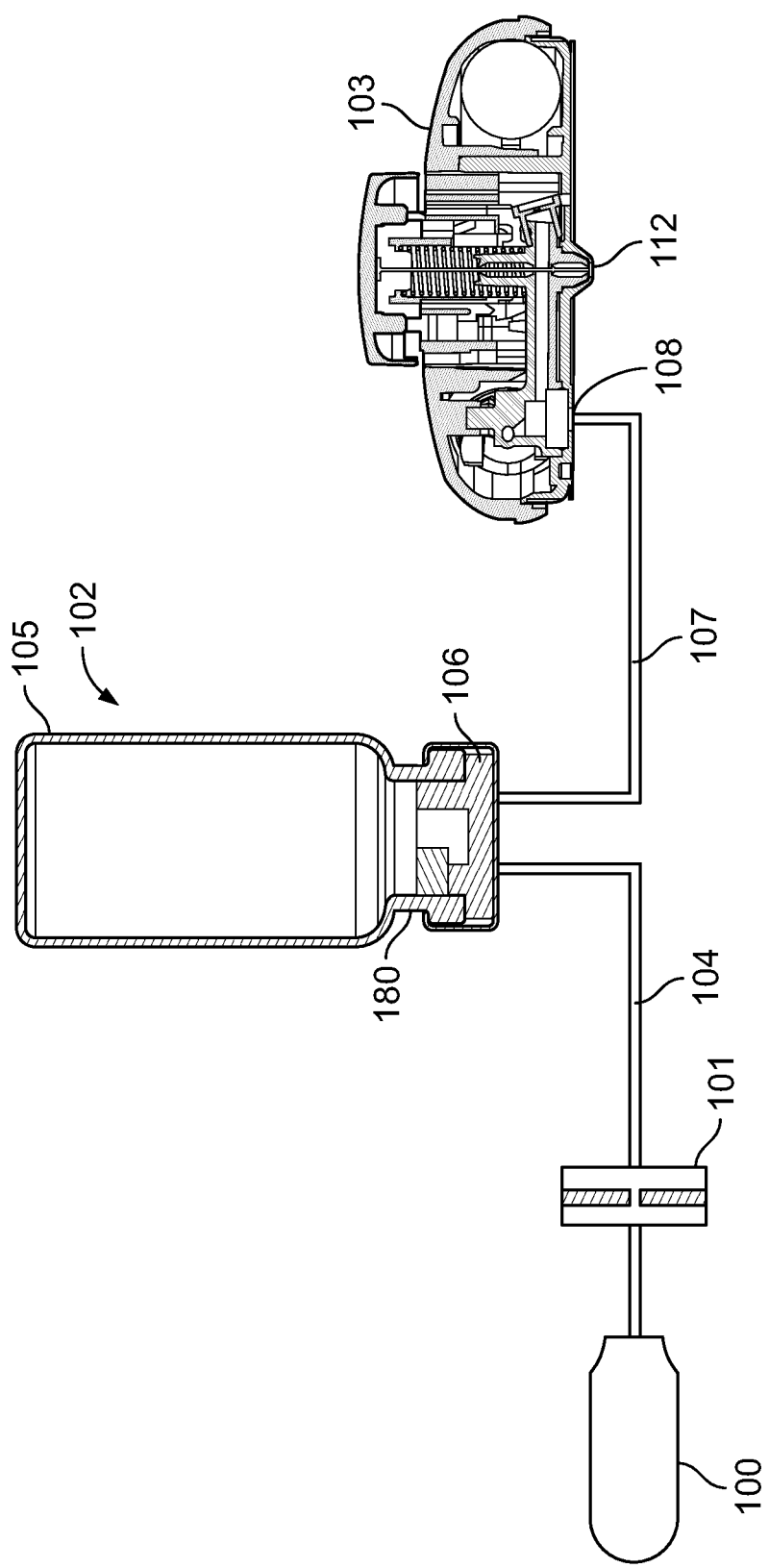
FIG. 1 is a schematic view of a single vial pressurized gas powered transfer system and an injection device.

As described in commonly assigned prior published PCT Application No. WO 2016/154413, which is hereby incorporated by reference herein in its entirety, FIG. 1 is a diagrammatic view of a single vial transfer system, including a pressure vessel in the form of a prefilled pressurized gas cylinder or cartridge 100, a flow restrictor and/or pressure regulator 101, a liquid medicament vial 102 and an injection device 103. The gas cylinder may be any suitable cylinder commercially available or may be a custom cylinder. For example, a variety of potential cylinders are available with high pressure gas filled disposable cylinders in capacities from 1 to 1000 cc. The cylinders may be charged to suitable pressures up to 2000-3000 psig or more. It is to be understood that relatively small capacity disposable cylinders will be suitable for the present subject matter. For example, the cylinder may have a volume of 10 ml or less, and more preferably less than 5 ml, such as 1-2 ml, pressurized to 500 psig or more, such as from 900 psig up to 2000-3000 psig or more.

The gas may be any suitable gas, such as, but not exclusively, an inert gas. As it will come in contact with medicament, the gas is preferably pathogen free—i.e., free of active pathogens. Nitrogen or argon may be suitable gases. When released from the cylinder, such as by puncture by a piercing pin, the gas is directed through a suitable flow path from the cylinder through the flow restrictor and/or pressure regulator 101 to the vial 102. Alternatively, the gas that exits the cylinder could be directed through a filter with pore size of 0.2 µm or less to filter the gas.

The flow restrictor and/or pressure regulator 101 may be of any suitable configuration. As an example only, in an embodiment of the disclosure described below, the flow restrictor and pressure regulator may take the form of a chamber formed in a device within which the cartridge is positioned and to which the vial 102 and injection device 103 are attached. From the restrictor/regulator, flow path 104 conducts the gas to the vial 102. The restrictor/regulator could take the form of a filter described above.

The vial 102 may be a standard drug vial with a rigid container portion 105 usually glass, open at one end and sealed by a piercable diaphragm or septum 106 of latex, silicone or other material. The present process is preferably carried out with the vial in an inverted vertical position so that the gas flows to the closed end of the vial, forcing essentially all the medicament from the vial under the force of the pressurized gas.

From the vial, flow path 107 directs the medicament under the pressure of the gas to a suitable vessel such as an injection device 103, an example of which is described in commonly assigned prior published PCT Application No. WO 2014/204894, noted previously. The injection device may have a liquid reservoir, such as an expandable reservoir for receiving the medicament, for example a reservoir that expands under pressure from the medicament. The reservoir may be biased to expel the medicament upon user actuation of the injection device once removed from the flow path 107. As an example only, the injector capacity can be 1-50 mL.

It should be noted that "injectable fluid," "injectable," "drug," "medicament" and like terms are used interchangeably herein.

The undersurface of the injection device 103 may include a filling port 108 and a dispense port 112. As illustrated in FIG. 1, the filling port 108 is the interface that allows the transfer apparatus filling path 107 to transfer liquid to the injection device 103. The filling port 108 preferably includes a check valve to prevent pressurized injectable from leaking out of the injection device 103 when the injection device is removed from the transfer apparatus and the filling port 108 is removed from the filling path 107.

The medicament is expelled from the injection device 103 via an injection cannula that passes through the dispense port 112.

Figure 2:
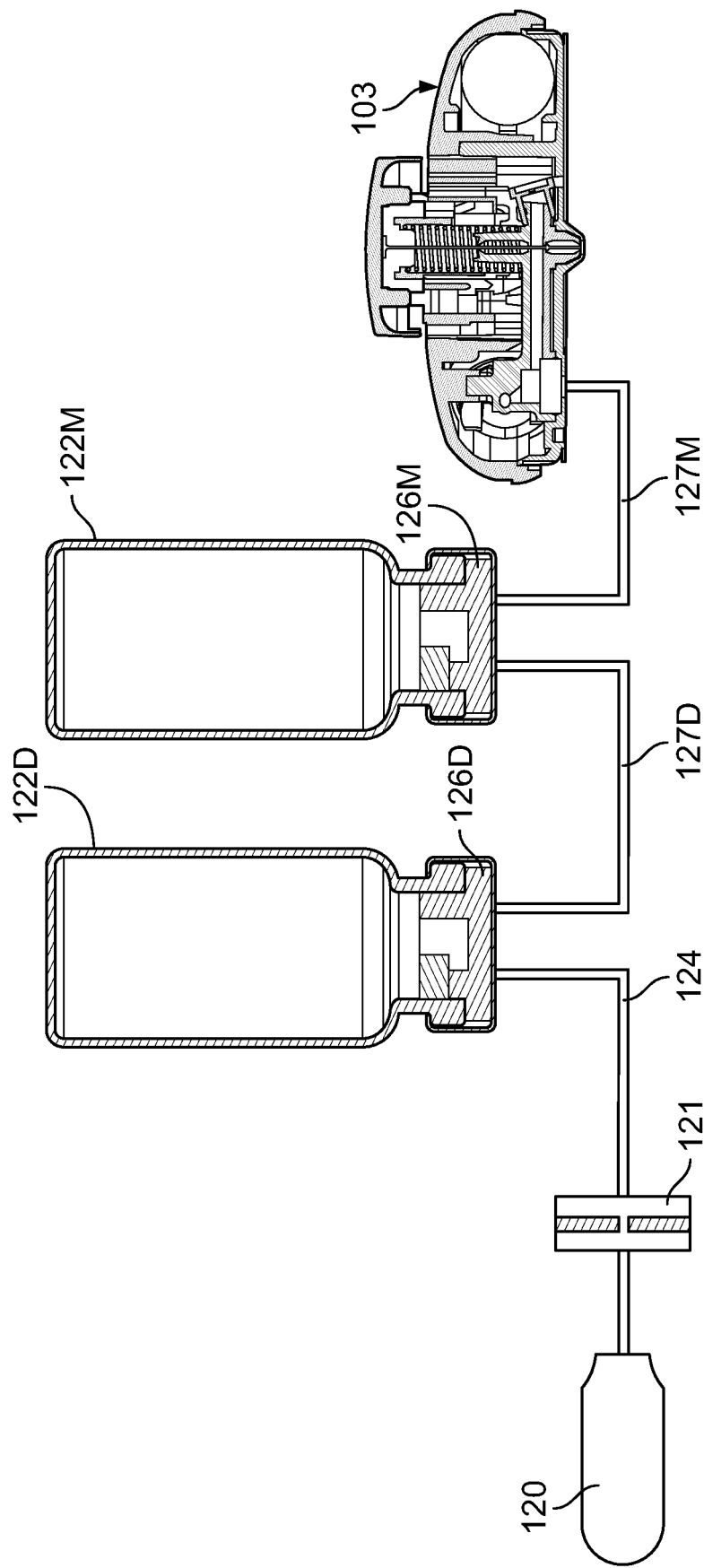
FIG. 2 is a schematic view of a dual vial pressurized gas powered transfer system and an injection device.

For purposes of illustration and not limitation, FIG. 2 is a diagrammatic view of a pressurized gas powered dual vial re-suspension and transfer system, including a pressure vessel in the form of a prefilled pressurized gas cylinder or cartridge 120, a flow restrictor and/or pressure regulator 121, a liquid diluent vial 122D, a medicament vial 122M and the injection device 103 of FIG. 1. (Each vial 122D and 122M could also contain liquid medicament). As in FIG. 1, the gas cylinder 120 may be any suitable cylinder commercially available or may be a custom cylinder.

Also similar to the single vial system, the gas may be any suitable gas, such as, but not exclusively, an inert gas preferably pathogen free—i.e., free of active pathogens. When released, such as by puncture by a piercing pin, the gas is directed through a suitable flowpath from the cylinder through the flow restrictor and/or pressure regulator 121 into the diluent vial 122D. Alternatively, the gas that exits the cylinder could be directed through a filter with pore size of 0.2 µm or less to filter the gas.

As in the system of FIG. 1, the flow restrictor and/or pressure regulator 121 may be of any suitable configuration, including a chamber formed in a device within which the cartridge is positioned and to which the vials 122D and 122M and injection device 103 are attached. From the restrictor/regulator, flow path 124 conducts the gas to the vial 122D. The restrictor/regulator could take the form of a filter described above.

The diluent (or first liquid medicament) vial 122D and medicament (or second liquid medicament) vial 122M may each be of standard drug vial configuration with a rigid container portion usually glass, open at one end and sealed by a piercable diaphragm or septum 126D and 126M of latex, silicone or other material. The present process is preferably carried out with the vials in inverted vertical position so that the gas flows to the closed end of the vials, forcing essentially all the diluent and/or medicament from the vials under the force of the pressurized gas, before any gas exits the medicament vial.

From the diluent (or first liquid medicament) vial 122D, flow path 127D directs the diluent (or liquid medicament) under the pressure of the gas into the medicament vial 122M, where it may re-suspend the medicament if in a dry of lyophilized form or dilute the medicament if in liquid concentrated form (or simply combine or mix with the medicament if in liquid non-concentrated form). From the medicament vial 122M, combined medicament and diluent or diluted or mixed liquid medicament flows through flow path 127M under the pressure of the gas to any suitable vessel, such as an injection device 103 as disclosed in the previously identified PCT application.

Figure 3A:
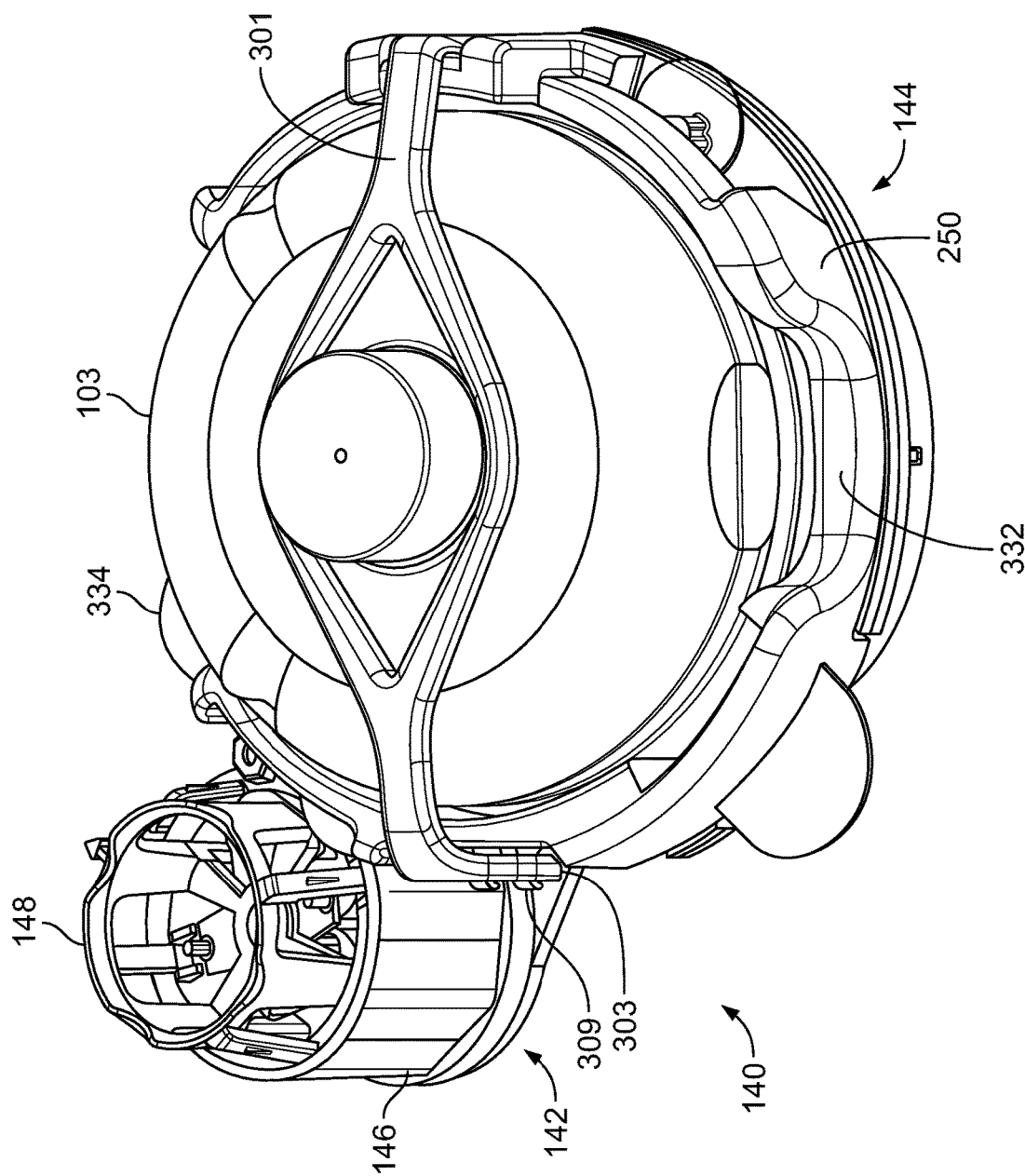
FIG. 3A is perspective view of an embodiment of the pressurized gas powered transfer device of the disclosure with an injection device attached.
Figure 3B:
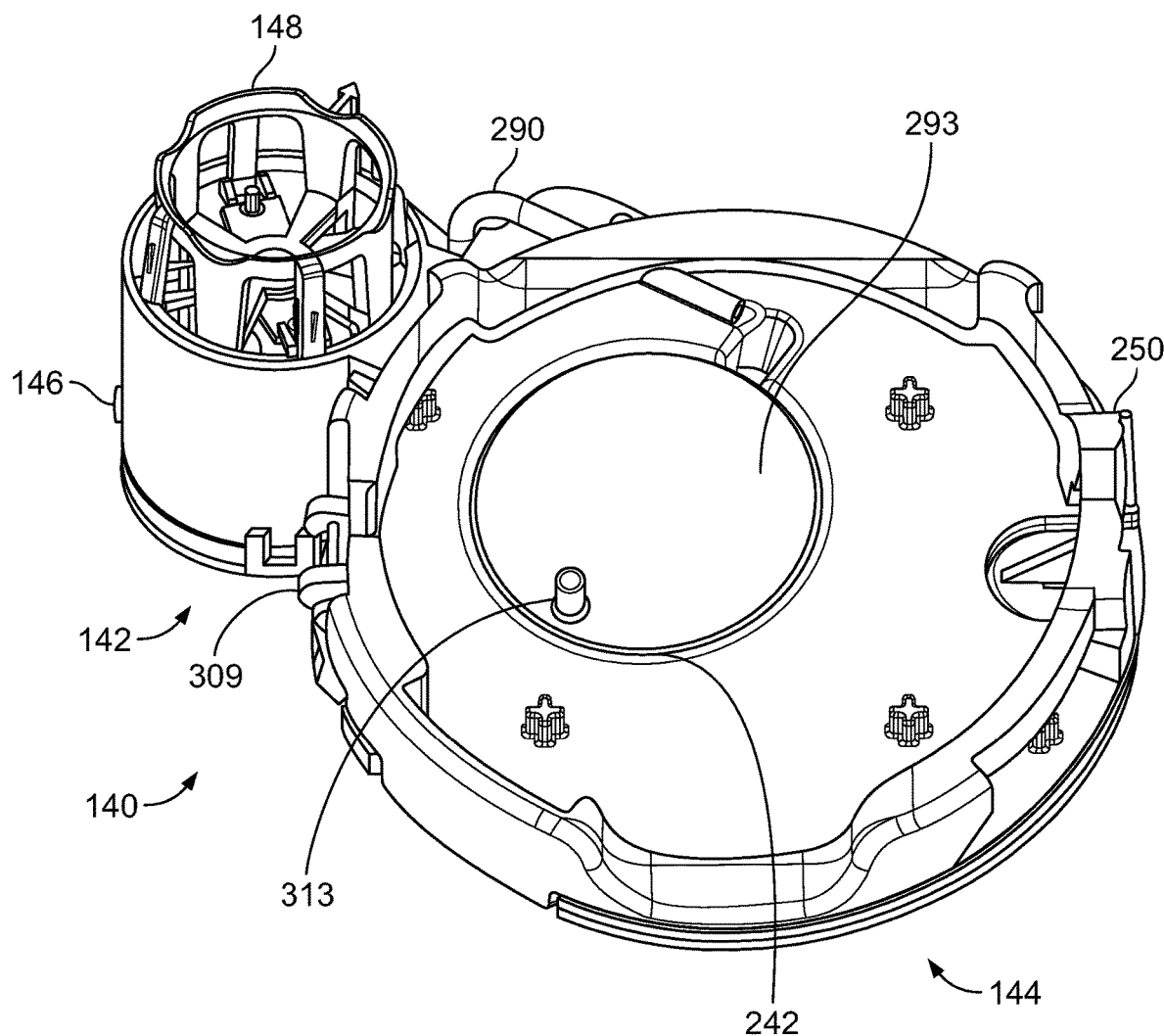
FIG. 3B is a perspective view of the pressurized gas powered transfer device of FIG. 3A with the injection device removed.

An embodiment of the pressurized gas powered transfer device of the disclosure is indicated in general at 140 in FIGS. 3A and 3B. The transfer device includes two main portions: (1) a vial holder, indicated in general at 142, and (2) a gas expansion chamber, indicated in general at 144. As illustrated in FIG. 3A and explained in greater detail below, an injection device 103 may be docked to the expansion chamber 144 to receive a liquid medicament.

While the embodiments disclosed below use a single vial, alternative embodiments include transfer stations that may accommodate two or more vials in the manner illustrated in FIG. 2.

In addition, while embodiments of the transfer device discussed below are single use, disposable devices, alternative embodiments include reusable transfer devices.

Figure 4:
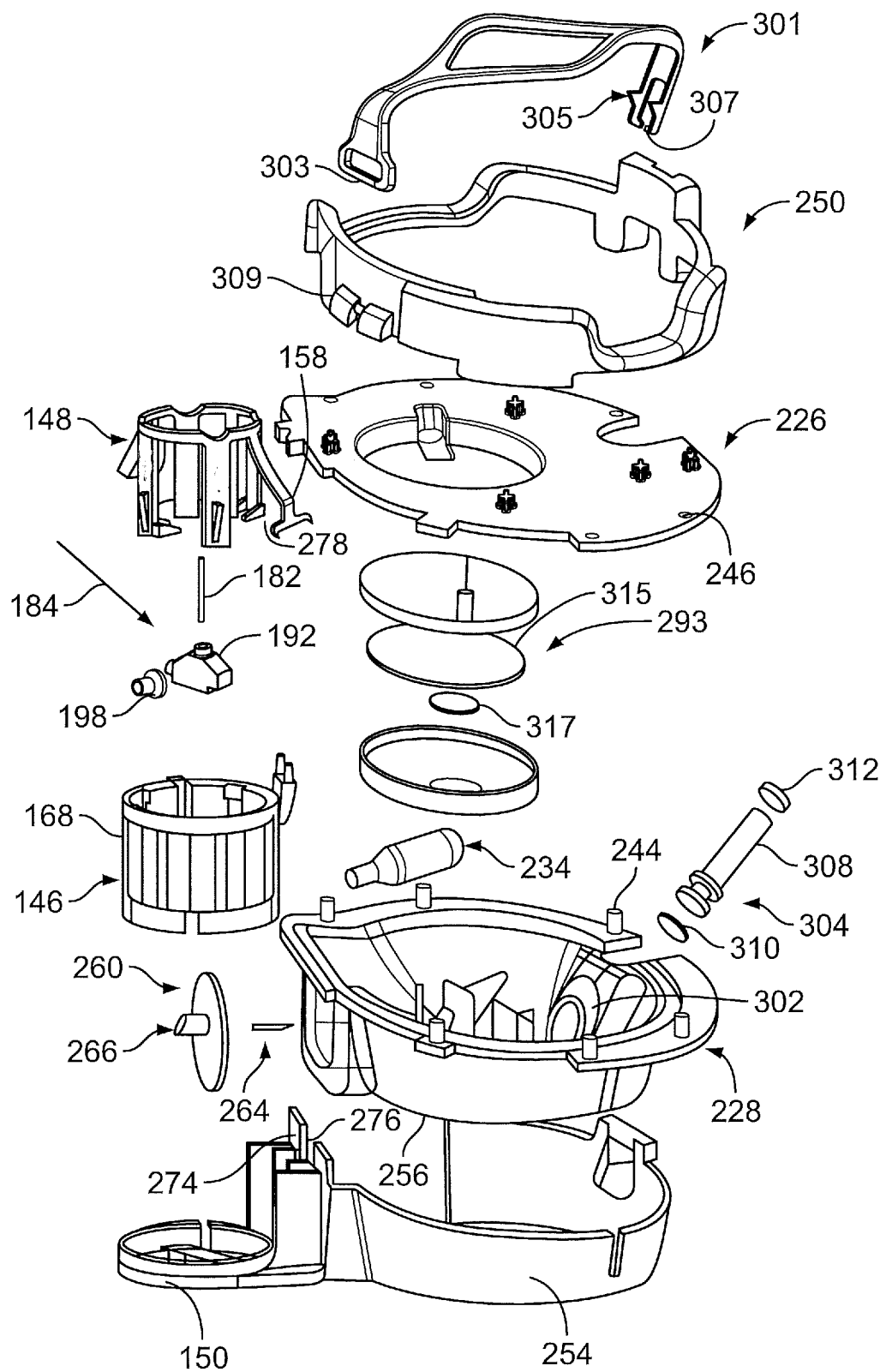
FIG. 4 is an exploded view of the pressurized gas powered transfer device of FIGS. 3A and 3B.
Figure 5A:
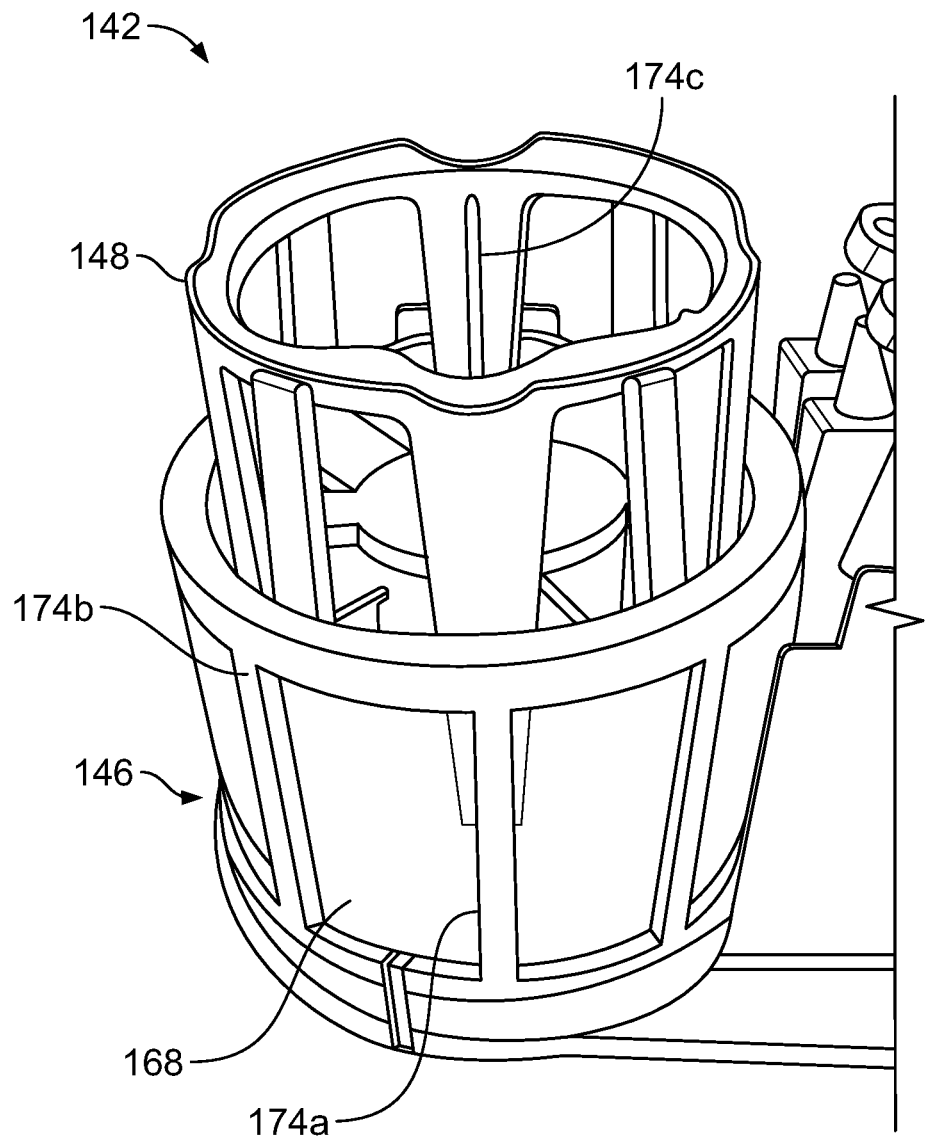
FIG. 5A is an enlarged perspective view of the vial holder of the pressurized gas powered transfer device of FIGS. 3A-4 with the vial elevator in the raised or extended position.
Figure 5B:
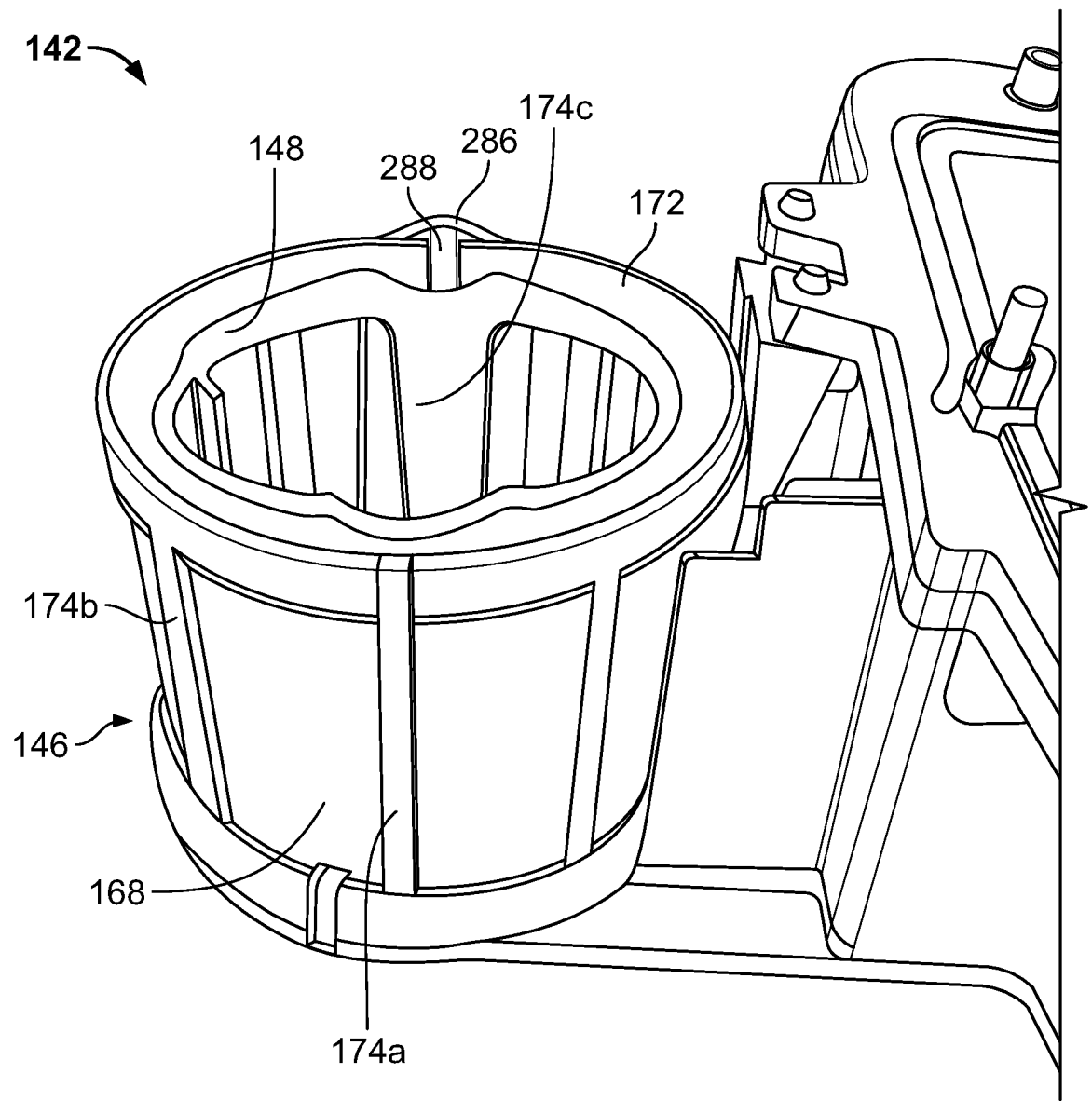
FIG. 5B is a perspective view of the vial holder of FIG. 5A with the vial elevator in the retracted or lowered position.

The vial holder 142 includes a vial elevator shaft, indicated in general at 146 in FIGS. 4, 5A and 5B, within which is received a vial elevator 148. The vial elevator shaft 146 is secured to a baseplate 150 (FIG. 4) of the transfer device. The vial elevator 148 vertically slides within the vial elevator shaft 146 in a telescoping fashion between an extended position, illustrated in FIG. 5A, and a retracted position, illustrated in FIG. 5B.

Figure 6:
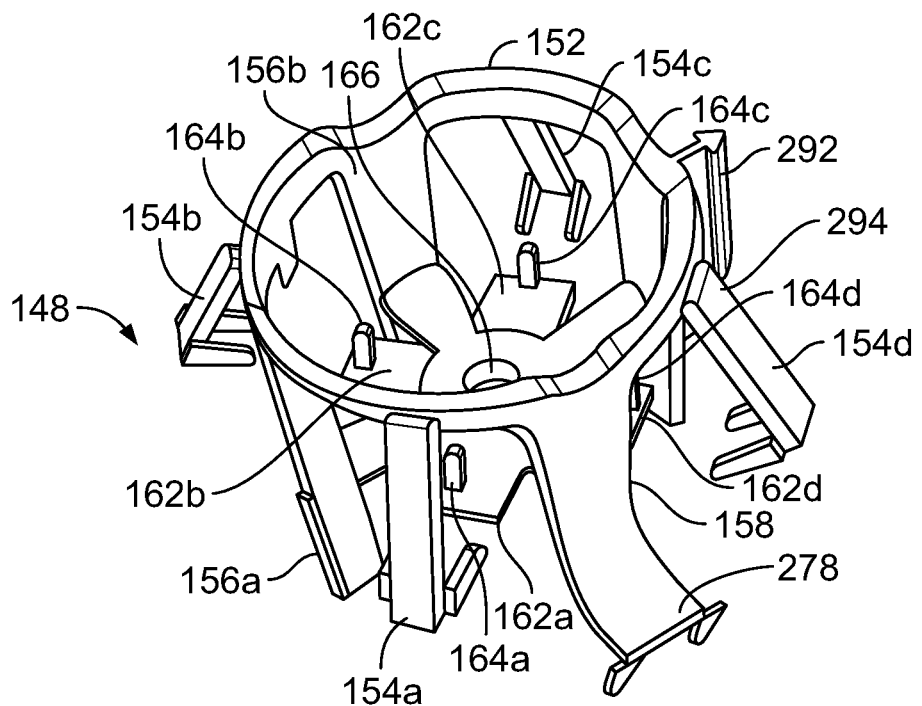
FIG. 6 is a perspective view of the vial elevator of the vial holder of FIGS. 5A and 5B.

As illustrated in FIG. 6, the vial elevator 148 includes a circular rim 152 from which lock arms 154a-154d downwardly extend. In addition, splines 156a and 156b (shown in FIG. 7 also) extend down from the rim 152, as does the actuation arm 158 for the pressurized gas cylinder piercing mechanism. Stop tabs 162a-162d radially extend from a central bottom portion of the elevator, and each features a stop pin 164a-164d. An opening 166 is formed in the center of the bottom of the vial elevator 148 and receives an upwardly pointing vial spike mounted to the bottom of the baseplate 150 (FIG. 4), as will be explained in greater detail below.

Figure 7:
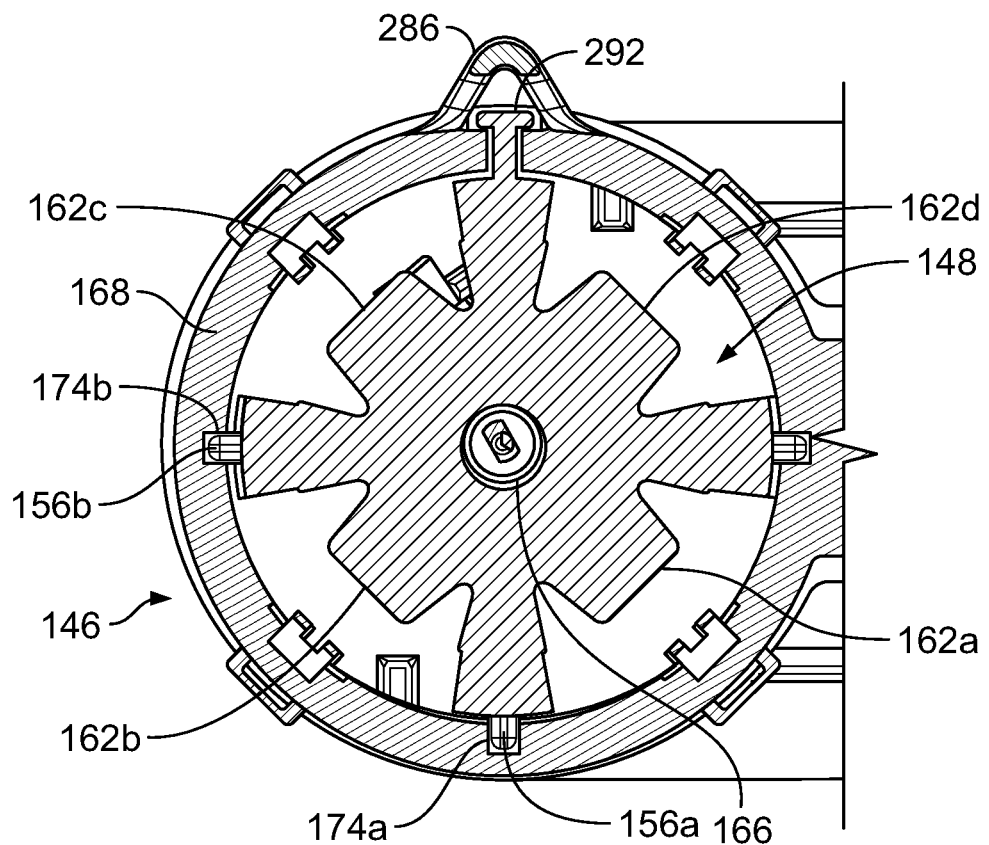
FIG. 7 is a cross-sectional view of the vial holder of FIGS. 5A-6 taken along a horizontal cutting plane.

As illustrated in FIG. 7, the vial elevator shaft 146 has a sidewall 168 that includes inwardly-facing channels 174a and 174b that receive the splines 156a and 156b of the vial elevator 148 in a sliding fashion to provide radial alignment of the vial elevator in the vial elevator shaft and to provide a smooth transition as the vial elevator moves.

Figure 8:
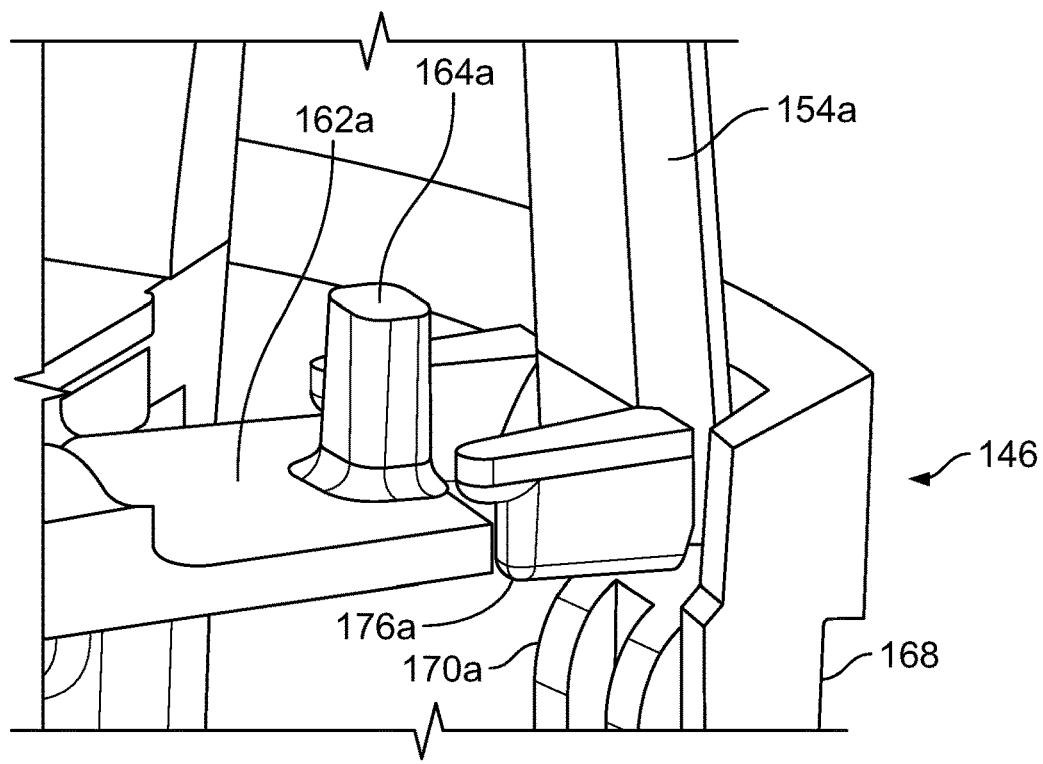
FIG. 8 is an enlarged perspective view of a stop tab, a stop pin, a locking arm and a locking claw of the vial elevator and the elevator shaft cam ramps of the vial elevator shaft of the vial holder of FIGS. 5A-7.

As illustrated for lock arm 154a in FIG. 8, the vial elevator shaft sidewall 168 also features an inwardly extending cam ramp 170a (FIG. 8). Similar cam ramps are provided for lock arms 154b-154d.

Figure 9:
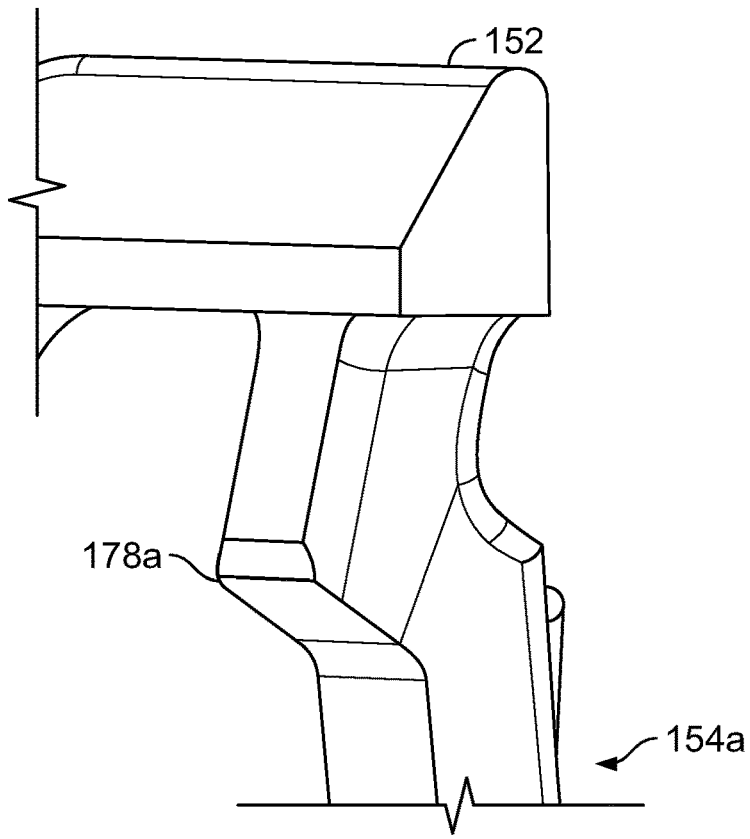
FIG. 9 is an enlarged perspective view of a locking shoulder of a locking arm of the vial elevator of FIGS. 5A-8.

As further illustrated in FIG. 8, the distal or lower end of the lock arm 154a includes a claw 176a, while the upper portion of the lock arm 154a includes, with reference to FIG. 9, a vial locking shoulder 178a. Lock arms 154b-154d feature similar structures.

In operation, a vial in an inverted orientation, as illustrated for vial 102 in FIG. 1, is lowered into the vial elevator 148 when the vial elevator is in the extended position (FIG. 5A) until the downward surface formed by the septum (106 of FIG. 1) or rim of the vial engages the stop pins 164a-164d (FIG. 6) of the stop tabs 162a-162d. The user then gently presses down on the vial, and the vial elevator 148 moves downwards into the vial elevator shaft 146 towards the retracted position illustrated in FIG. 5B.

As the vial elevator 146 moves downwards towards the retracted position illustrated in FIG. 5B, the claws (176a of FIG. 8) on the distal ends of the lock arms 154a-154d are moved inwards due to the urging of the elevator shaft cam ramps (170a of FIG. 8). As this occurs, the distal ends of the stop tabs 162a-162d of the vial elevator 148 are pushed downwards due to the downward-facing end surface (septum and/or vial rim) of the vial pushing downwards on the stop pins 164a-164d. When the vial elevator 148 reaches the retracted position illustrated in FIG. 5B, the vial locking shoulders (178a of FIG. 9) of the lock arms 154a-154d have moved into a position where they engage the neck (180 of FIG. 1) of the vial 102. As a result, the vial is locked within the vial holder 142.

As an example only, each vial can have a capacity of 1-50 mL with neck finishes of 13-20 mm.

If a user attempts to push the vial elevator 148 of FIGS. 4-6 down into the vial elevator shaft 146 of FIGS. 4-5B without a vial in the vial elevator, the inwardly traveling claws (176a of FIG. 8) on the distal ends of the lock arms 154a-154d will engage the distal ends of the stop tabs 162a-162d, as illustrated in FIG. 8, so as to prevent the vial elevator 148 from being moved into the retracted position of FIG. 5B. The spacing of the bottom of the baseplate (150 of FIG. 4) from the bottom of the vial elevator 148 is such that when the claws of the lock arms are in engagement with the stop tabs, the tip of the vial spike positioned on the bottom of the vial holder base is below the bottom of the vial elevator (i.e., the upwardly-pointing vial spike has not yet passed through the opening 166 of the elevator bottom). As a result, the user is protected from sticking his or her finger with the vial spike.

As noted previously, and illustrated in FIGS. 4, 10 and 11, a vial spike 182 is mounted to the bottom of the baseplate 150 via a vial spike hub 184. The vial spike features a tip that is pointed so as to pass through the vial diaphragm or septum (106 in FIGS. 1, 12B and 12C) and has two fluid paths—one to permit entry of compressed gas to force the liquid out of the vial, and one for the exiting liquid to the injection device.

Figure 11:
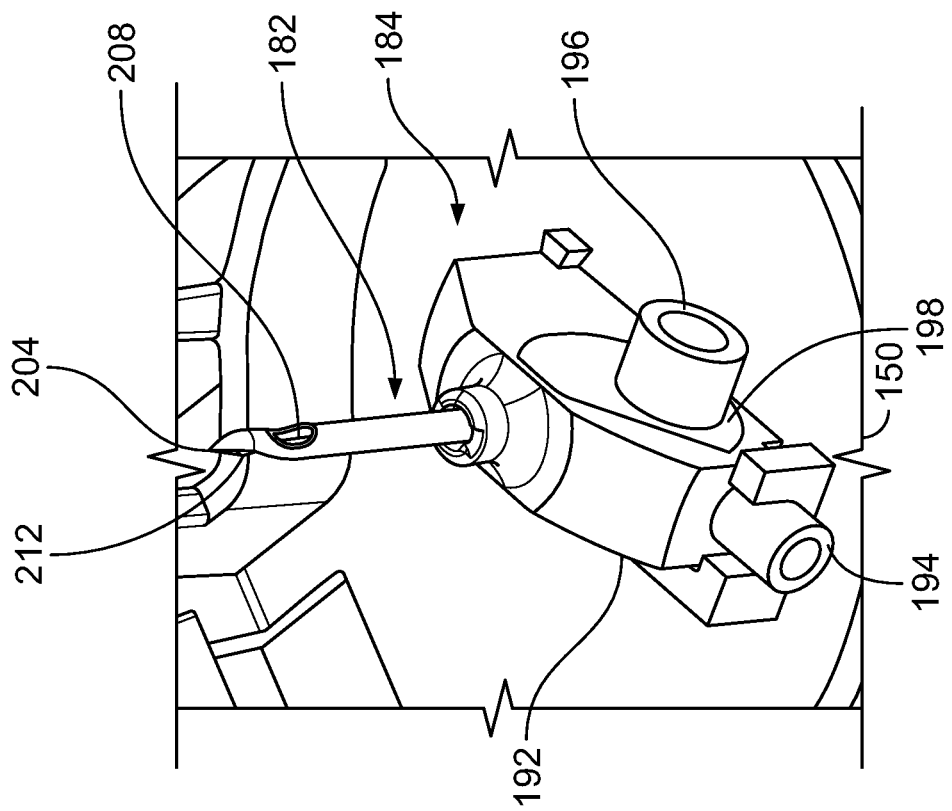
FIG. 11 is a second perspective view of a vial spike hub assembly of the injection device of FIGS. 3A-4.
Figure 10:
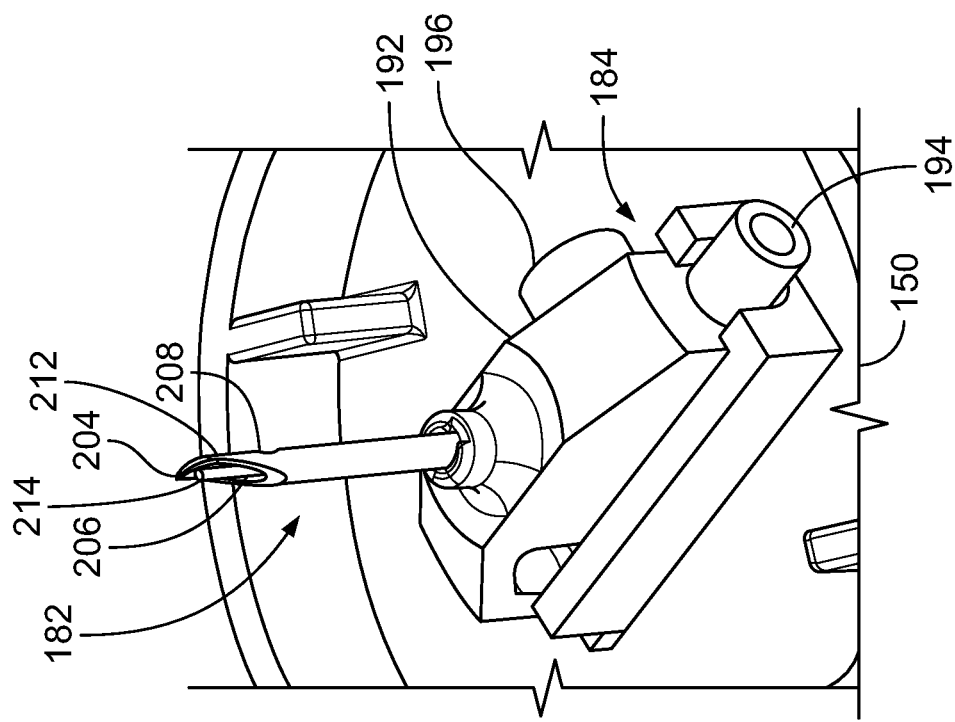
FIG. 10 is a first perspective view of a vial spike hub assembly of the injection device of FIGS. 3A-4.

As illustrated in FIGS. 4, 10 and 11, the vial spike hub 184 includes a housing 192 having a gas inlet fitting 194 and a fluid outlet fitting 196. The fluid outlet fitting may optionally be included in a hub cap 198 that is secured to the housing 192 to provide access to a cavity (202 of FIGS. 12A-12C) of the housing during assembly.

As illustrated in FIGS. 10-12C, the vial spike 182 may take the form of a cannula, which is preferably constructed from stainless steel, having a pointed tip 204 and liquid openings 206 and 208. A semi-flexible gas tube 212, which is preferably constructed from polyamide, features a gas outlet opening 214 and extends through the vial spike 182 and the cavity 202 and gas inlet fitting 194 of the vial spike hub. As will be explained in greater detail below, the lower end of the gas tube 212 is selectively in fluid communication with a source of pressurized air or gas.

Figure 12B:
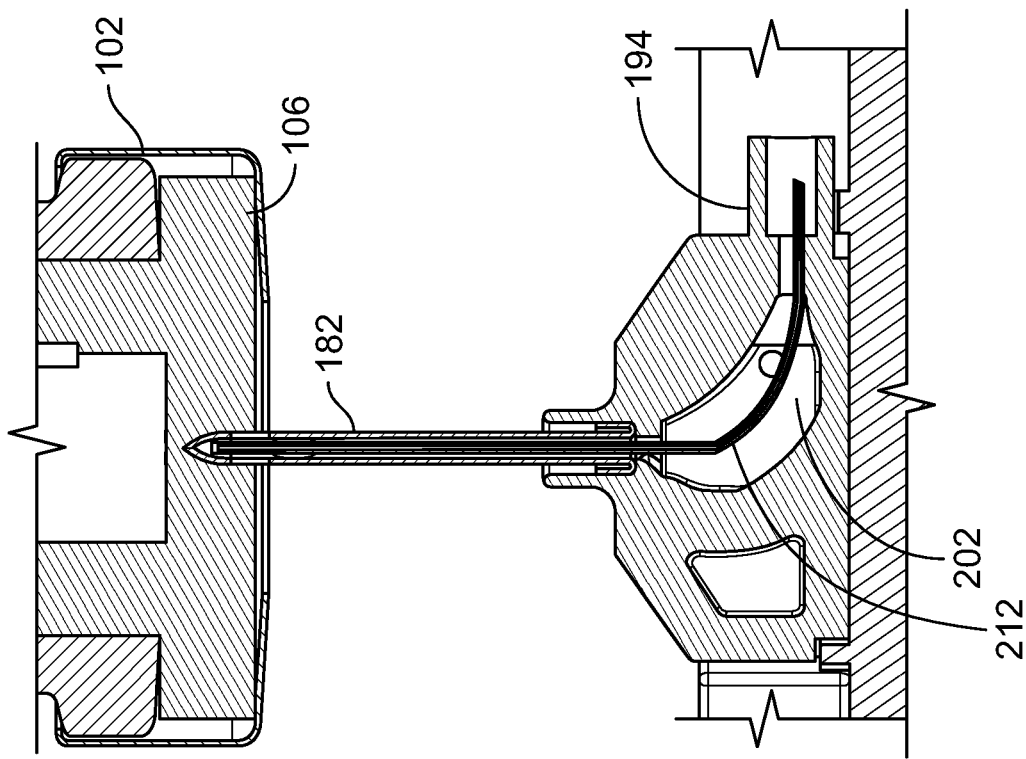
FIG. 12B is a side elevational view of the vial spike hub assembly of FIG. 12A during initial insertion of the vial spike into a vial.
Figure 12A:
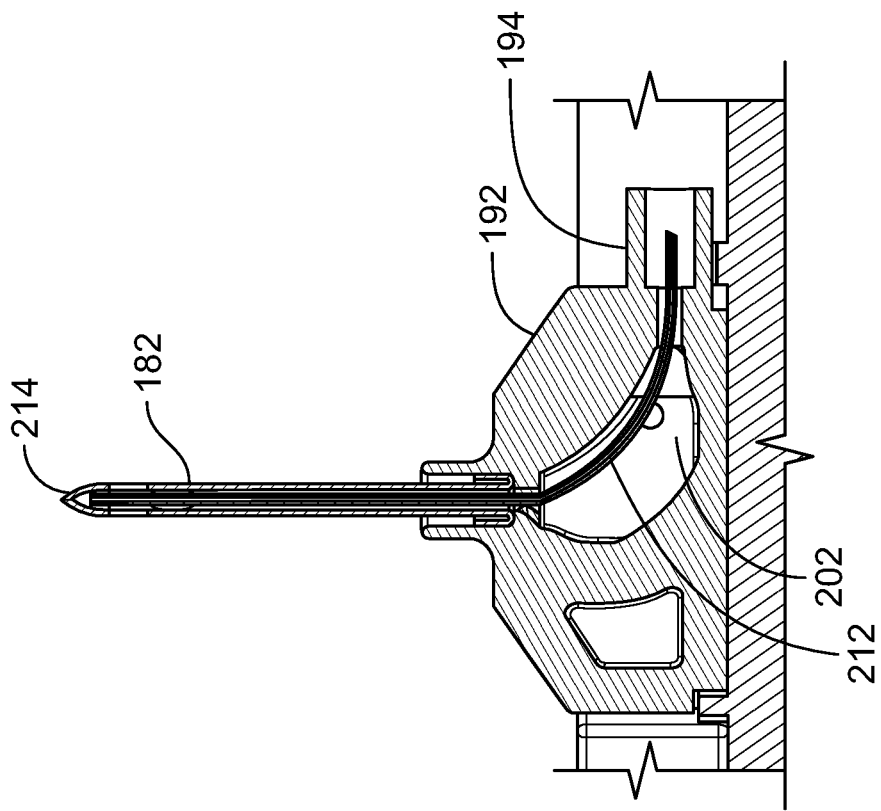
FIG. 12A is a side elevational view of the vial spike hub assembly of FIGS. 10 and 11 with the hub cap removed prior to insertion of the vial spike into a vial.
Figure 12C:
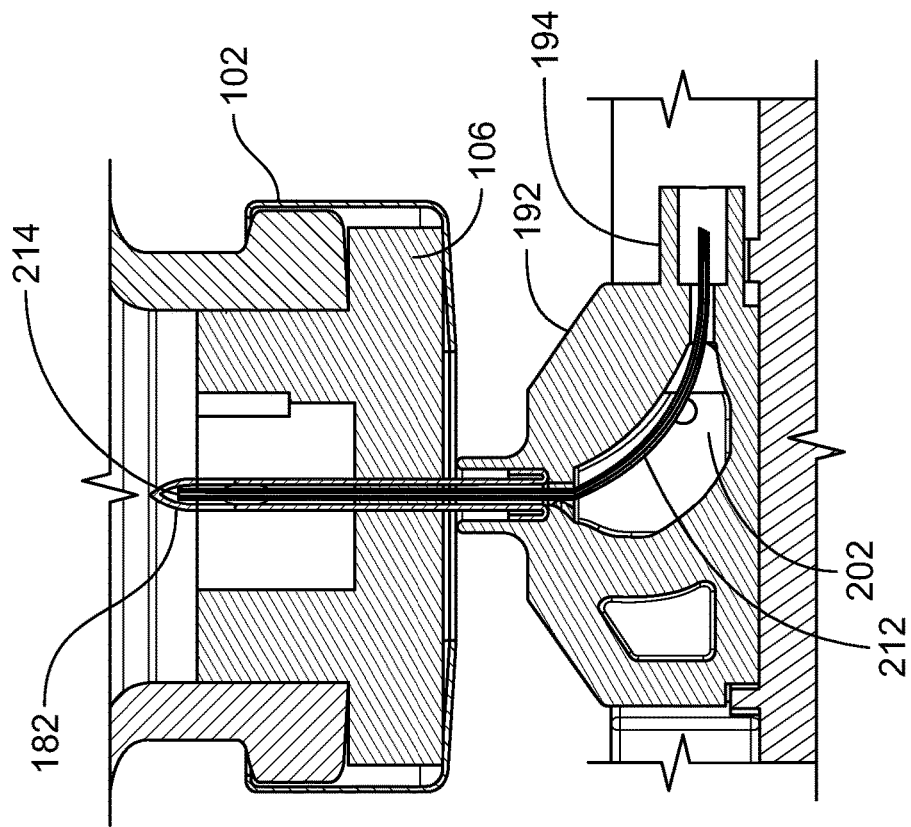
FIG. 12C is a side elevational view of the vial spike hub assembly of FIGS. 12A and 12B with the vial spike fully inserted into the vial.

In order for incoming gas from the gas tube 212 to reach the headspace of a vial, such as vial 102 of FIGS. 12B and 12C, it should be able to pass by the liquid openings 206 and 208 of the vial spike and reach the top surface of the liquid drug in the vial. As a result, as illustrated in FIGS. 10 and 11, the gas tube opening 214 is positioned generally higher than the liquid openings 206 and 208 of the vial spike 182 when the pressurized gas is introduced into the vial.

To keep the gas tube 212 from buckling or being bent by the diaphragm or septum (106 of FIGS. 12B and 12C) of the vial as the vial spike 182 is moved there through, the cavity 202 allows the gas tube 212 to flex in the vial spike hub housing 192. More specifically, with reference to FIG. 12A, prior to insertion of the vial spike 182 into a vial, the gas tube 212 is in a natural, extended position, with the gas outlet opening 214 reaching just beneath the pointed tip 214 of the vial spike 182.

With reference to FIG. 12B, as the vial spike 182 is being inserted into the septum 106, the upper end of the gas tube 212 is forced down inside the vial spike 182 by the septum, where it is protected against bending and buckling. The gas tube 212 has a column strength that biases it to want to remain straight when no external forces are applied to it. As illustrated in FIG. 12B, these properties allow the gas tube 212 to flex down in the cavity 202 of the housing 192 of the vial spike hub when a downward force is applied to the tip of the tubing (the force applied by the vial septum 106 in FIG. 12B). Since the gas tube 212 has an affinity to remain straight, it springs back to its original, extended position, as illustrated in FIG. 12C, after the force of the vial septum 106 is off of the top end of the gas tube 212 and transferred to the vial spike 182 as the septum becomes seated on the vial spike.

After the vial spike and gas tube are fully positioned within the vial, pressurized air is released into the vial headspace through the gas tube and gas tube opening. The tip of the gas tube (in its extended position) featuring the gas outlet opening is generally higher than the fluid outlet openings in the vial spike, thus allowing the air to bubble up through the liquid drug and into the headspace or closed end of the vial.

Figure 13:
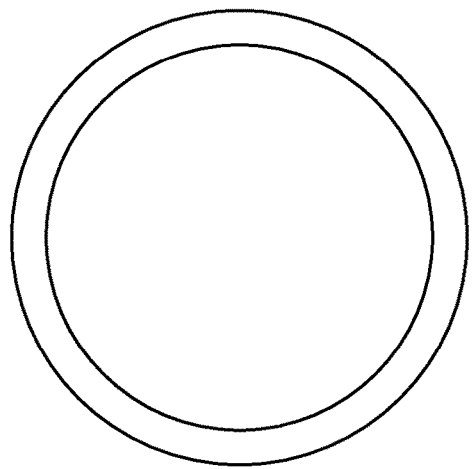
FIG. 13 is a cross-sectional view of the gas tube of the vial spike hub assembly of FIGS. 10 and 11 prior to crimping.
Figure 14:
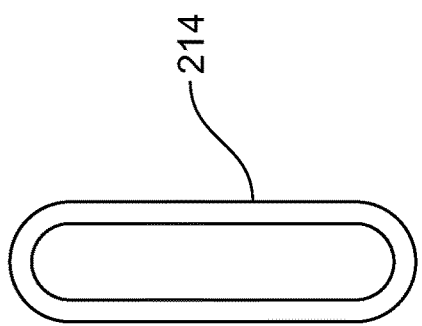
FIG. 14 is a cross-sectional view of the gas tube of the vial spike hub assembly of FIGS. 10 and 11 after crimping.

An optional feature of the gas tube 212 that aids in the gas reaching the top of the vial is the shape of the gas tube opening 214 at the tip of the gas tube. Rather than a circular opening shape (FIG. 13) the gas tube 212 is pinched at the tip to create a thin, long ovular shape for the gas tube opening 214 (FIG. 14). This shape acts as a restriction at the outlet point of the tube, which in turn causes the gas to be released at higher velocities from the tube, which prevents the gas from having a chance to be drawn into the liquid flow pathways in the vial spike. This concept is best described as being similar to someone restricting the water flow out of a garden hose by placing their thumb/finger over the outlet—doing this increases the velocity of the fluid stream leaving the tube.

As the pressurized gas is introduced into the headspace of the vial, the liquid in the vial is forced to exit through the vial spike liquid outlets 206 and 208 of FIGS. 10 and 11. This liquid travels down into the cavity 202 (FIGS. 12A-12C) of the vial spike hub and out through fluid outlet fitting 196 (FIGS. 10 and 11). The residual fluid in this sub-assembly should be reduced as much as possible. In order to do this, the fluid outlet fitting 196 is positioned near the bottom of the cavity 202.

Figure 15:
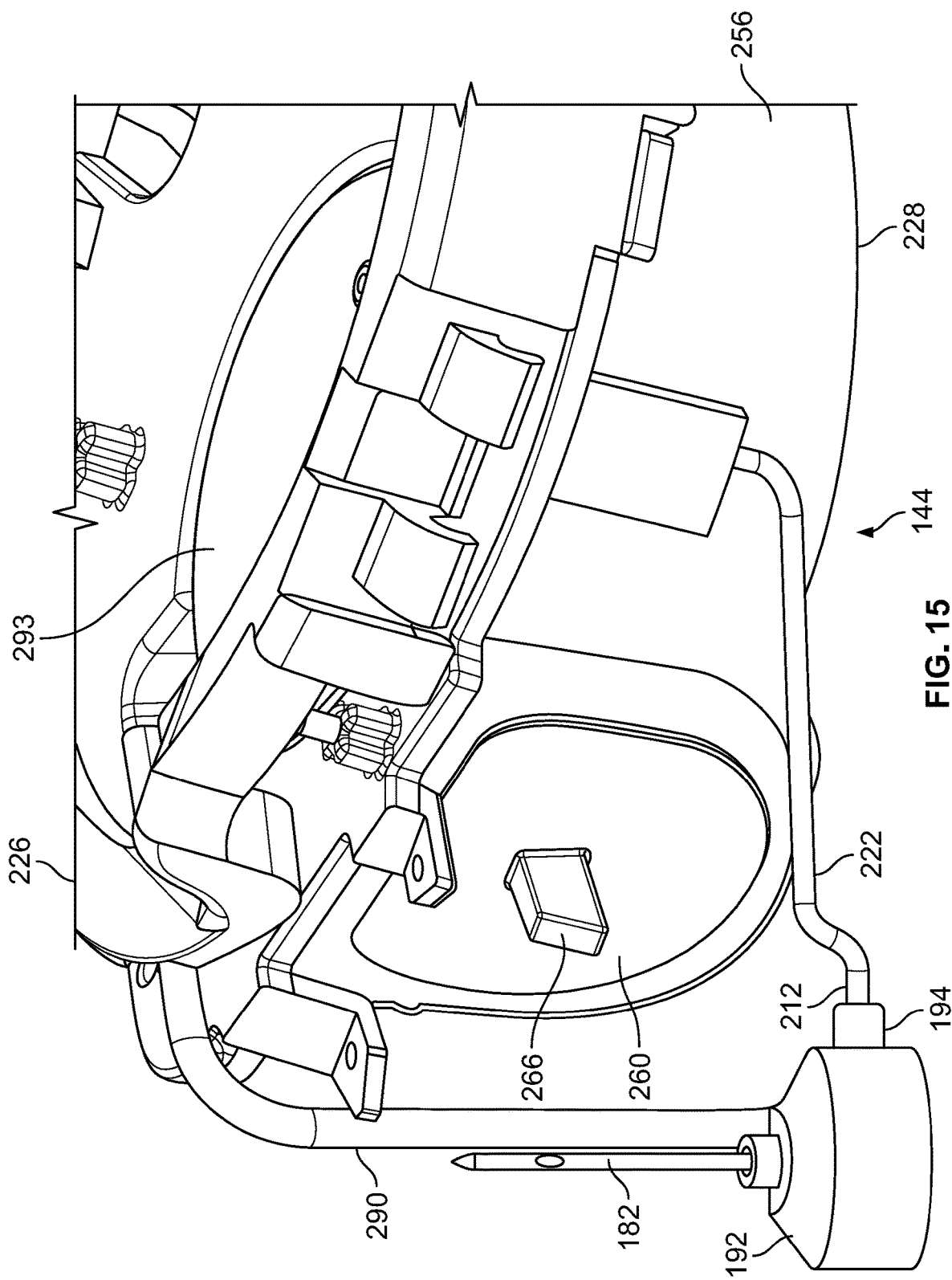
FIG. 15 is a first perspective view of the vial hub assembly and the pressurized gas extension chamber of the transfer device of FIGS. 3A-4.
Figure 16:
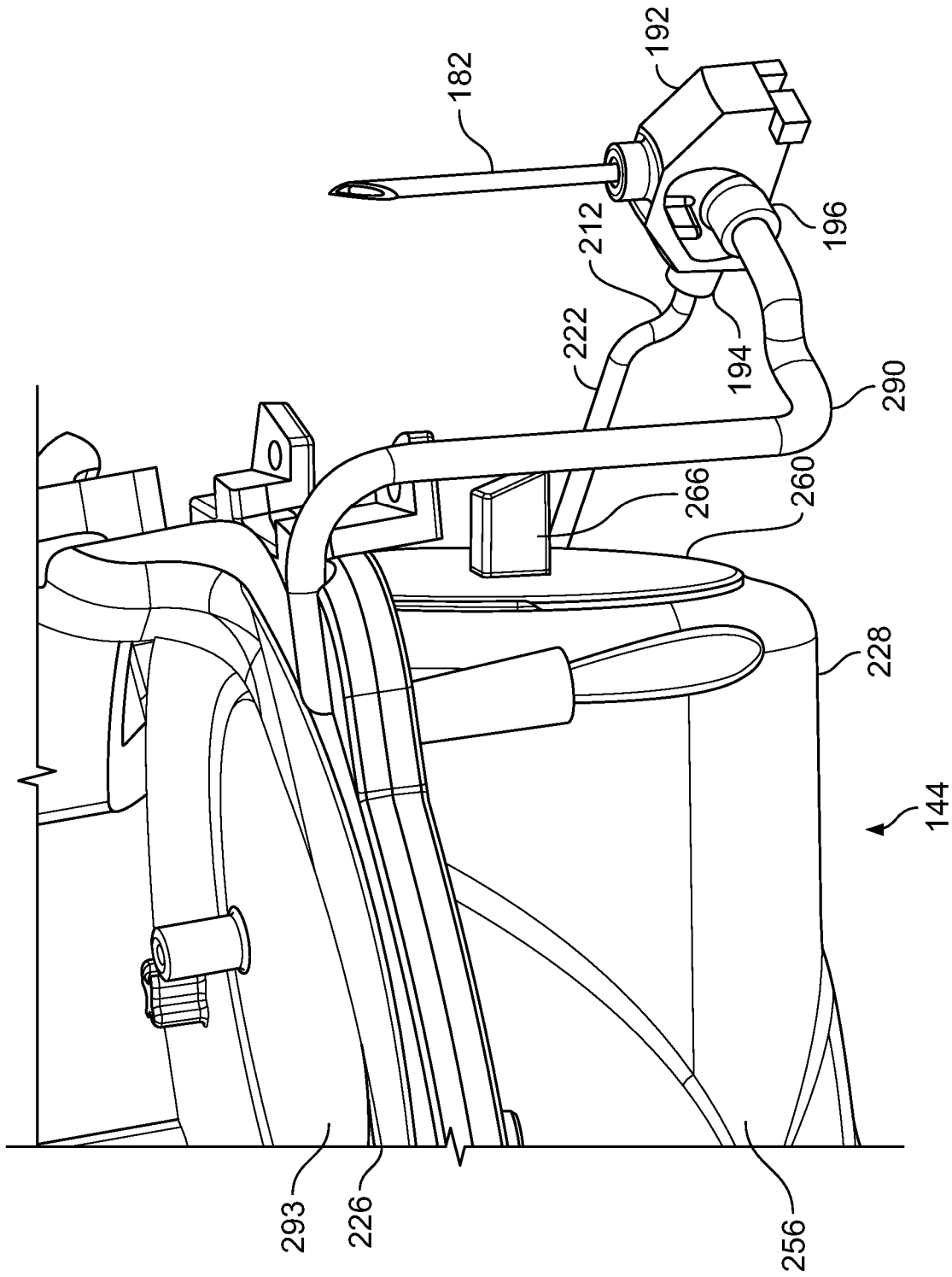
FIG. 16 is a second perspective view of the vial hub assembly and the pressurized gas extension chamber of the transfer device of FIGS. 3A-4.

With reference to FIGS. 15 and 16, the gas tube 212 passing through the gas inlet fitting 194 (or merely the cavity 202) of the housing 192 of the vial spike hub is joined or spliced to flexible transfer tubing 222. The opposite end of the transfer tubing 222 is connected to a gas expansion chamber, indicated in general at 144, which serves as a source of pressurized gas for pressurizing the vial in the manner described above.

As illustrated in FIGS. 4, 15-17, the gas expansion chamber 144 includes an expansion chamber top 226 and an expansion chamber bottom 228. As illustrated in FIG. 15, the transfer tubing 222 is connected to a pressurized gas supply port of the gas expansion chamber 144. As is illustrated in FIG. 4, the expansion chamber bottom 228 is received by the transfer device baseplate 150.

Figure 17:
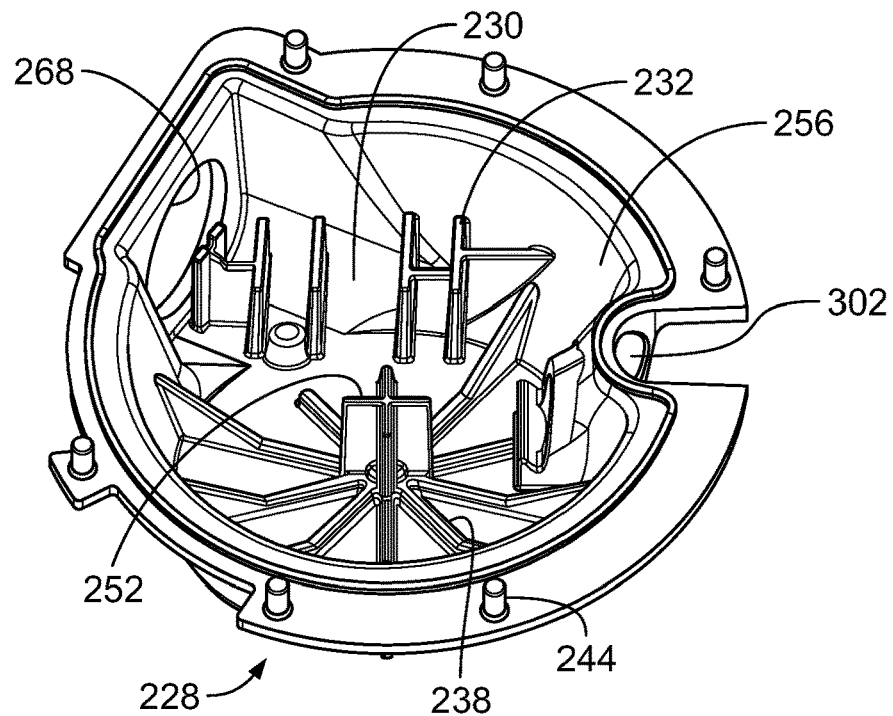
FIG. 17 is a perspective view of the chamber bottom of the pressurized gas expansion chamber of the transfer device of FIGS. 3A-4.
Figure 18:
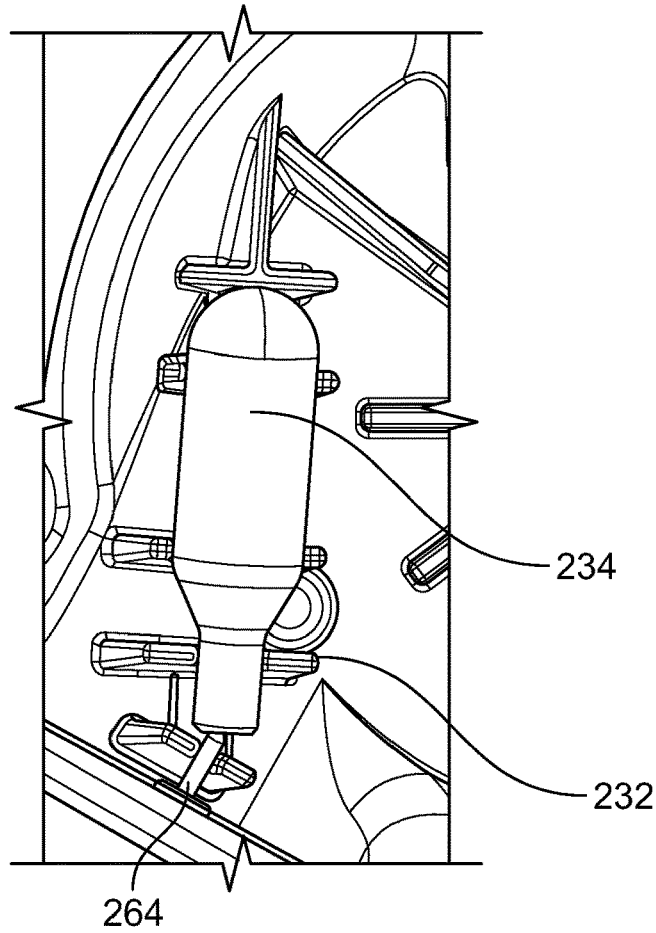
FIG. 18 is an enlarged perspective view showing a pressurized gas canister positioned with the chamber bottom of FIG. 17.

With reference to FIGS. 17 and 18, the expansion chamber bottom 228 defines an expansion chamber interior cavity 230 and is provided with brackets 232 configured to retain and support a gas cartridge 234 (also shown in FIG. 4) containing a compressed gas, such as compressed nitrogen. Of course cartridges containing other types of compressed or pressurized gases may be used.

Figure 19:
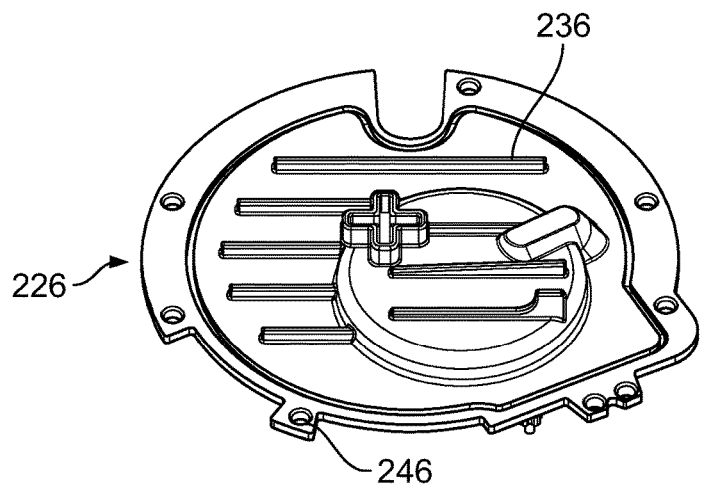
FIG. 19 is a top perspective view of the chamber top of the pressurized gas expansion chamber of the transfer device of FIGS. 3A-4.
Figure 20:
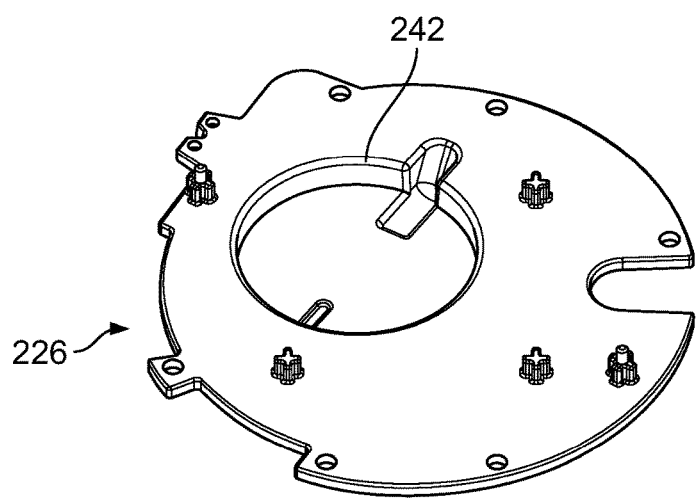
FIG. 20 is a bottom perspective view of the chamber top of the pressurized gas expansion chamber of the transfer device of FIGS. 3A-4.

As illustrated in FIGS. 17 and 19, ribs 236 and 238 are formed on the bottom surface of the chamber top 226 and the chamber bottom 228, respectively, and support the chamber to restrict deflection or burst. The top surface of the chamber top 226, illustrated in FIG. 20, is provided with a recess 242 for holding a filter through which, as explained in greater detail below, fluid travels from the vial spike hub to an injection device mounted to the transfer device.

Chamber posts 244 (FIG. 17) on the rim of the chamber bottom 228 align with openings formed in tabs 246 (FIG. 19) extending from the chamber top 226 as they are being assembled (also shown in FIG. 4). The chamber top and bottom may then be glued together with adhesive. The chamber posts 244 also mate with hex holes on the retention ring, illustrated at 250 in FIG. 4, to keep it attached to the device. An X-post, indicated at 252 in FIG. 17, allows for an additional gluing surface and does not allow the large surface area of the chamber top 226 to bow out when the interior cavity (230 of FIG. 17) of the gas expansion chamber is pressurized. A flexible wall support, indicated at 254 of FIG. 4, of the baseplate 150 provides extra support for the gas expansion chamber sidewall 256 (FIGS. 4 and 15-17) when the gas expansion chamber is pressurized.

The interior cavity 230 of the expansion chamber 144 is pressurized when the gas cartridge 234 (FIGS. 4 and 18) positioned therein is punctured. The cartridge puncture mechanism for doing so will now be described.

With reference to FIGS. 4, 15, 16, 21 and 22, a flexible wall 260 features an inner surface that holds a puncture tip 264, having a sharp point, and an outer surface that is provided with a flexible wall cam ramp 266. As an example only, the flexible wall 160 may be constructed of plastic with a thickness of approximately 0.030" for flexibility.

Figure 21:
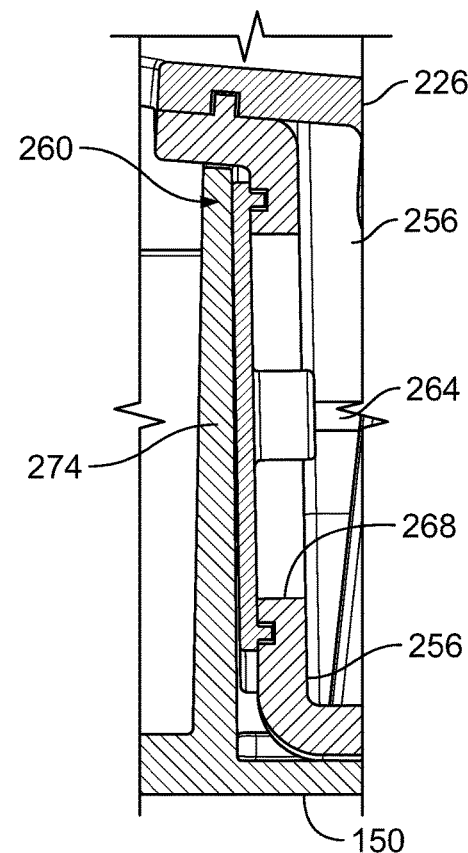
FIG. 21 is an enlarged cross-sectional view of the gas cartridge piercing mechanism of the transfer device of FIGS. 3A-4.
Figure 22:
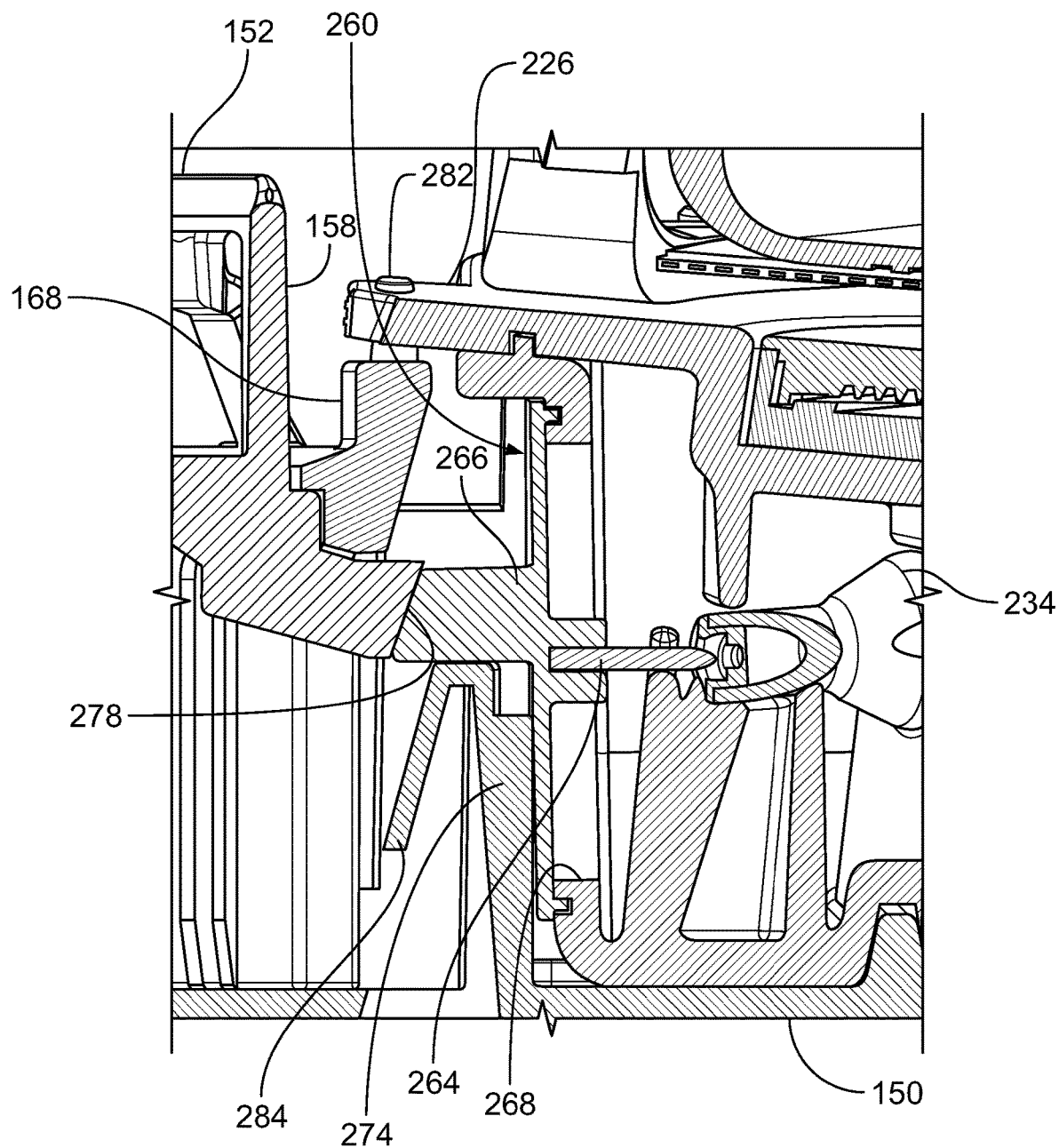
FIG. 22 is a second cross-sectional view of the gas cartridge piercing mechanism of the transfer device of FIGS. 3A-4.

The flexible wall 260 is positioned over an opening, indicated at 268 in FIGS. 17, 21 and 22, with the puncture tip 264 passing there through, as illustrated in FIGS. 21 and 22. The flexible wall is glued in position with adhesive and then sandwiched between a support rib 274 (FIGS. 4, 21 and 22) formed on baseplate 150 after the transfer device is assembled. With reference to FIG. 4, the support rib 274 features a vertical slot 276 that accommodates the flexible wall cam ramp 266.

As described previously with reference to FIG. 6, an actuation arm 158 extends down from the rim 152 of the vial elevator 148. This is also shown in FIG. 22. As shown in FIGS. 4, 6, 22 and 23 the distal end of the actuation arm 158 is provided with an elevator cam ramp 278.

Figure 23:
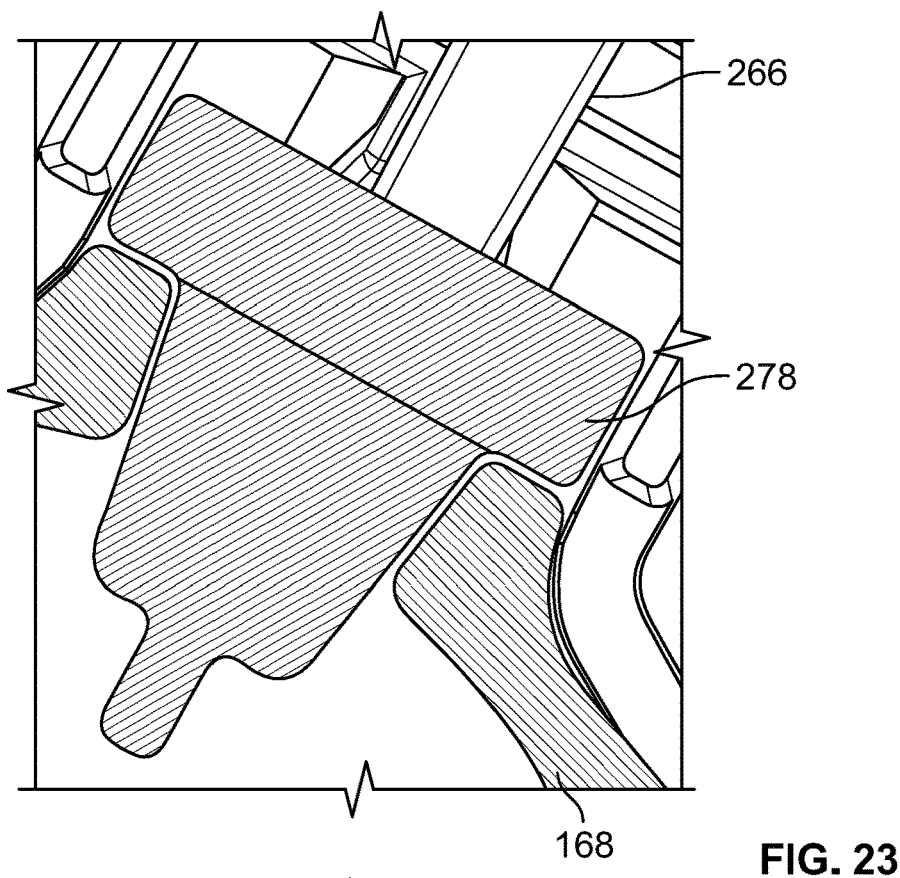
FIG. 23 is an enlarged top plan view of the elevator and flexible wall cam ramps of the gas cartridge piercing mechanism of FIGS. 21 and 22.

As a vial is inserted in the vial elevator (148 of FIGS. 4-6), and pushed down so that the vial elevator retracts into the vial elevator shaft (146 of FIGS. 4-5B), the actuation arm 158 of the vial elevator moves down so that, with reference to FIGS. 22 and 23, the elevator cam ramp 278 interacts with the flexible wall cam ramp 266 so as to force the central portion of the flexible wall 260, and thus the puncture tip 264, to move inwards and puncture the end of the pressurized gas cartridge 234 (also shown in FIG. 18). In doing so, the flexible wall elastically deforms in a concave fashion (when viewed from outside of the gas expansion chamber 144). The flexible wall cam ram 266 and the elevator cam ramp each preferably features a 20 degree angle (from vertical) to reduce the force and displacement needed to flex, and thus move the central portion of, the flexible wall 260.

The shape and volume of the internal cavity 230 (FIG. 17) of the gas expansion chamber 144 are such that the pressure of the gas provided to the transfer tubing 222, and thus to the vial spike hub and vial, is less than the pressure of the gas in the gas cartridge 234 (FIG. 18). As a result, the internal cavity 230 acts as a pressure regulator.

With reference to FIG. 22, the elevator shaft wall 168 features a pin 282 that is received by an opening formed in the chamber top 226 so that the elevator shaft is linked to the expansion chamber so as to restrict any movement from the top of the elevator shaft to help ensure puncture of the gas cartridge.

The support rib 274 of the baseplate 150 restricts the vertical movement of the flexible wall cam ramp 266 which helps eliminate any slack that would cause a misfire.

As illustrated in FIGS. 18 and 22, the angle at which the puncture tip 264 engages the pressurized gas cartridge 234 is preferably such that it forces the puncture tip into the corner of the cartridge puncture zone, that is, where the thinnest walls of the cartridge are producing the smallest puncture loads.

Figure 24:
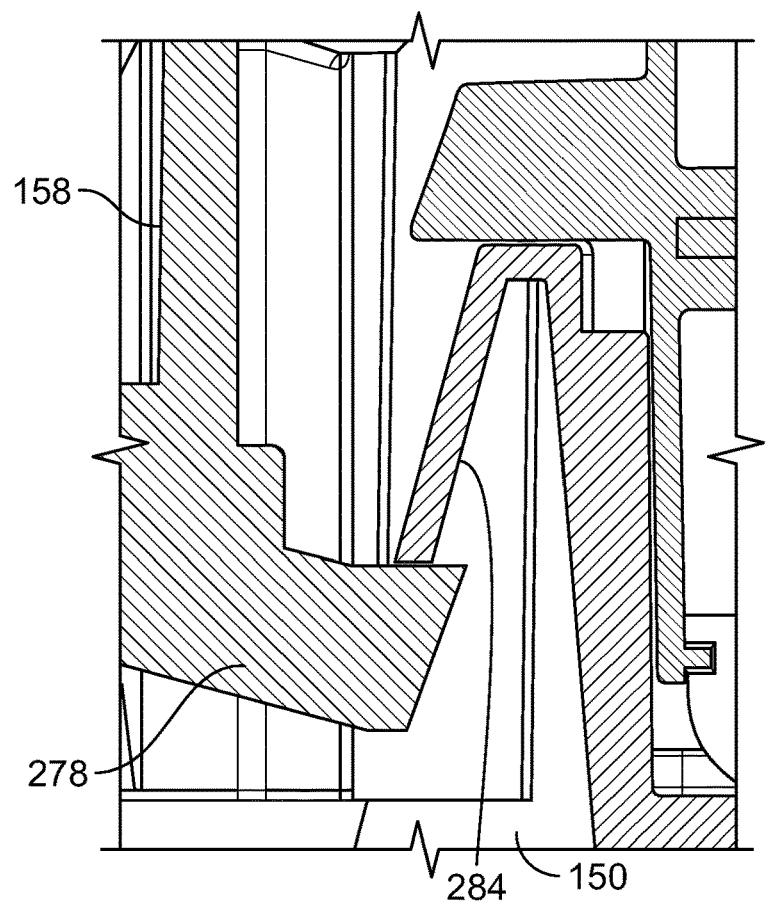
FIG. 24 is an enlarged cross sectional view showing the elevator cam ramp of the vial elevator engaging the locking tab of the base plate.

As illustrated in FIGS. 22 and 24, the baseplate also features an elevator locking tab 284 that flexes out of the way as the vial elevator is retracted into the vial elevator shaft and the vial elevator cam ramp 278 passes over it. The elevator locking tab 284 then flexes back over the elevator cam ramp 278, as illustrated in FIG. 24, to prevent removal of the vial from the vial elevator after the transfer of the vial contents has commenced.

A tube pinch extension, indicated at 286 in FIGS. 5B, 7, 25, 26A and 26B, defines a slot 288 on elevator shaft that acts as a holding position for the transfer tubing 222 (FIGS. 15, 16, 26A and 26B), which extends between the pressurized gas expansion chamber and the gas tube of the vial spike hub.

Figure 25:
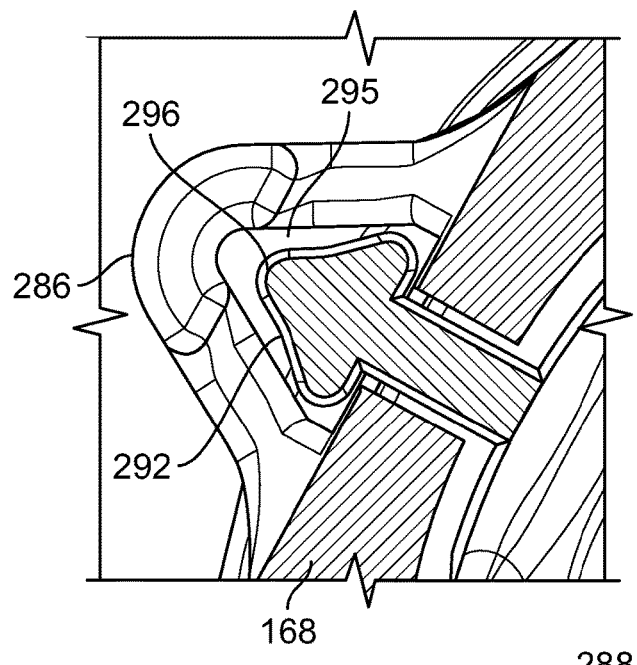
FIG. 25 is an enlarged top plan view of the pinch tube extension and blade of the vial holder of the transfer device of FIGS. 3A-4.
Figure 26A:
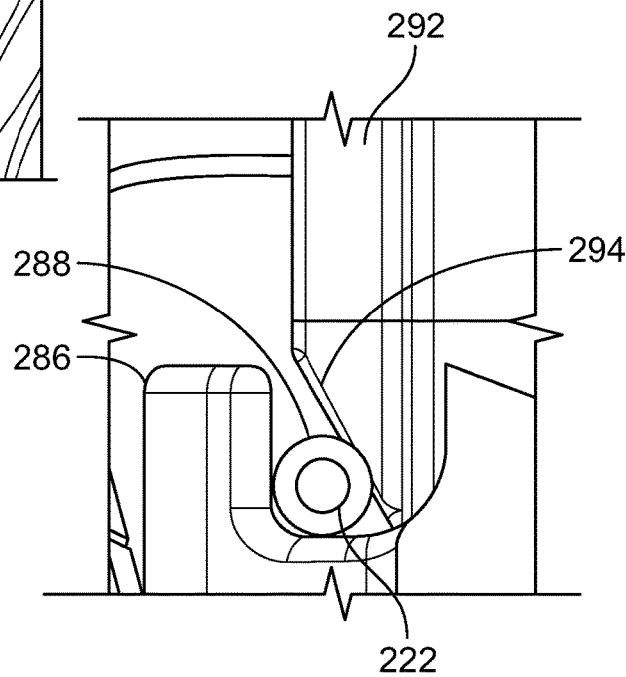
FIG. 26A is an enlarged side elevation view of the pinch tube blade of FIG. 25 beginning to engage the transfer tubing of the transfer device of FIGS. 3A-4.

The vial elevator includes a tube pinch blade, indicated at 292 in FIGS. 6, 7, 25, 26A and 26B, having a ramped bottom surface, indicated at 294 in FIGS. 6 and 26A. The tube pinch blade 292 passes through a corresponding opening (295 of FIG. 25) of the tube pinch extension.

Figure 26B:
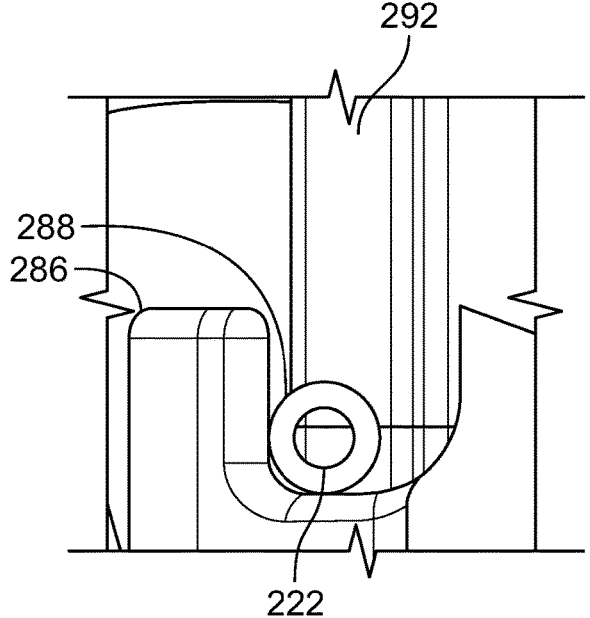
FIG. 26B is an enlarged side elevation view of the pinch tube blade of FIG. 25 engaging the transfer tubing of the transfer device of FIGS. 3A-4.

As illustrated in FIGS. 26A and 26B, as the vial elevator and vial move down towards the retracted position in the vial elevator shaft, the tube pinch blade 292 travels through the pinch tube extension 286 and pinches the transfer tubing 222 against the edge defining the slot 288 slot of the pinch tube extension until the vial elevator is in the fully retracted position (FIG. 5B). An aspect of the system is the timing in which the gas cylinder is punctured and gas introduction into the vial. As the vial is inserted into the elevator and pushed to the end of travel, the elevator interacts with the flexible wall to puncture the gas canister. It is desirable for the vial spike be in the vial before flow of the pressurized gas into the vial. By pinching the tube during travel of the elevator and puncture of the gas canister, there is no flow of pressurized gas into the vial until the vial spike is completely inserted into the vial (i.e. when the vial elevator is in the fully retracted position of FIG. 5B). As illustrated in FIG. 25, the pinch blade 292 preferably features an arrowhead shape, where the point (296 of FIG. 25) of the arrowhead pinches the tube and the arrowhead rear flats oppose the normal force to pinch the tube by the abutting the corresponding side of opening 295.

The transfer tubing 222 is preferably constructed of tubing that is rigid enough that it can be pinched and released without interfering with air flow. As an example only, the transfer tubing 222 may be PVC or other compatible tubing with a 0.030" inner diameter and a 0.060" outer diameter.

As explained previously, liquid in a vial is forced by pressurized gas to exit through the vial spike, vial spike hub cavity 202 (FIGS. 12A-12C) and out through fluid outlet fitting 196 (FIGS. 15 and 16) of the vial spike hub. As illustrated in FIGS. 15 and 16 (and 3B), a fluid transfer line 290 directs fluid from the fluid outlet fitting 296 to a vent filter, indicated at 293 in FIGS. 3B, 15 and 16. A schematic representation of the vent filter is presented in FIG. 27, where the vent filter is indicated in general at 293.

The vent filter is used to vent the front end and back end air from the system during the transfer of drug, keeping air from entering the injection device. More specifically, as explained above, a pressurized canister is punctured and is used as the driving force to push liquid and air from a vial. The empty fluid transfer line 290 between the vial spike hub and the vent filter 293 is filled with front end air that should be vented from the system before liquid can be pushed into the injection device.

Figure 27:
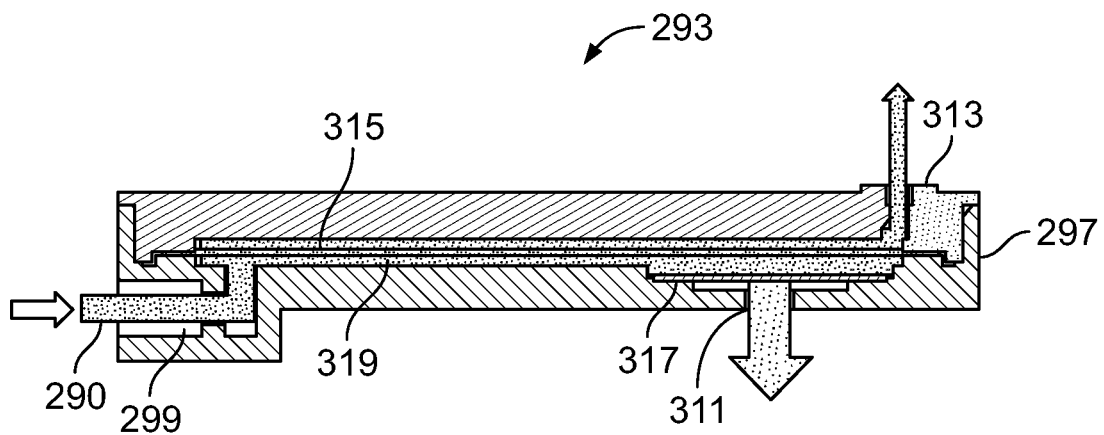
FIG. 27 is a cross-sectional view of the vent filter of the transfer device of FIGS. 3A-4 taken along a vertical cutting plane.

With reference to FIG. 27, the vent filter includes a housing 297 having fluid inlet port 299, to which the fluid transfer line 290 is connected, an air outlet port 311 and a liquid outlet port 313 (also shown in FIG. 3B), to which the filling port of the injection device (103 of FIG. 3A) connects to receive liquid. The housing also contains a hydrophilic membrane 315 and a hydrophobic membrane 317, with a fluid chamber 319 positioned there between. The fluid chamber 319 receives fluid from the fluid transfer line 290. As a result, the front end air trapped in the fluid path passes through the hydrophobic membrane 317 and out of the air outlet port 311 and into the atmosphere. The filtered liquid passes through the hydrophilic membrane 315, out through the liquid outlet portion 313 and into the injection device.

The front end air is vented due to the inherent flow restriction of the hydrophilic membrane 315, coupled with the pressure required to fill the injection device. These factors force the front end air to find the path of least resistance when being sent through the vent filter 293, and that is through the hydrophobic membrane 317 and through air outlet port 311 rather than through the restricted hydrophilic membrane 315 and into the injection device. The hydrophilic membrane of the vent filter allows liquid to pass through it and enter the injection device. Once the hydrophilic membrane is wetted by the liquid, it will not allow air to pass through it, only liquid, thus keeping the air from entering the injection device. The hydrophilic filter also has the capability of not only filtering air but also aggregate or particulate from the drug product from being transferred into the injection device.

Once all of the liquid is transferred to the injection device, residual air pressure still exists in the transfer device, including in the expansion chamber. This air enters the filter and is blocked by the hydrophilic membrane 315 and exits out of the vent filter 293 into the atmosphere through the hydrophobic membrane 317. This process continues until a specified pressure is reached within the interior cavity of the gas expansion chamber, and a pressure relief assembly, described below, vents the remaining pressure in the system.

The pore size of the hydrophilic membrane 315 is preferably set by the differential pressure of the transfer system and the internal pressure of the injection device. If the pressure gets higher than what the vent filter 293 can handle, it will allow air into the injection device.

The liquid outlet port 313 may optionally receive a cannula to aid in the filling of the injection device. As an example only, the cannula may be a 19 gauge needle having a curled tip that reduces the risk of damaging a fill septum of the injection device.

As noted previously with reference to FIG. 20, the top surface of the chamber top 226 is provided with a recess 242 for holding the vent filter 293 (as illustrated in FIG. 3B). This helps in reducing the overall height of the system.

With reference to FIG. 3A, a retainer strap 301 holds the injection device 103 on the transfer device 140 during transportation. In addition, the retainer strap 301 is intended to remain latched during the transfer of drug from the vial to the injection device 103. Once all of the drug is transferred to the injection device, the retainer strap 301 is released automatically, showing the user that the injection device is ready to be placed on the body. In addition, a final venting from the transfer device is performed that releases residual pressure inside the gas expansion chamber that remains after the drug has been completely transferred to the injection device. This feature prevents the user from removing the injection device from the transfer base too early. Without the strap, the user may be tempted to remove the injection device before all of the drug has been transferred out of the vial. The mechanism that performs these functions will now be described.

Figure 28:
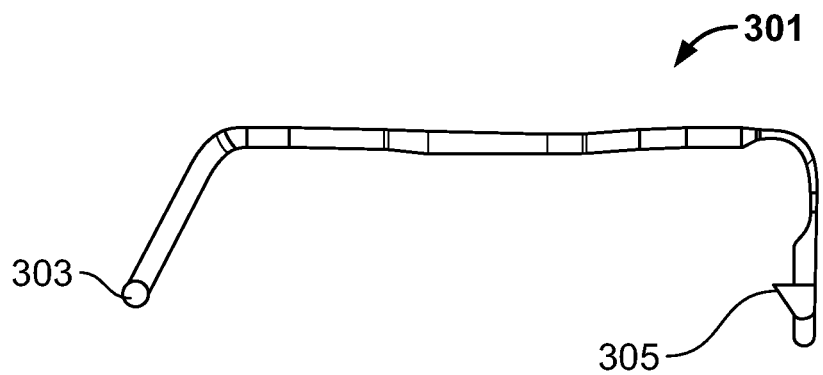
FIG. 28 is a side elevational view of the retainer strap of the transfer device of FIGS. 3A-4.
Figure 29:
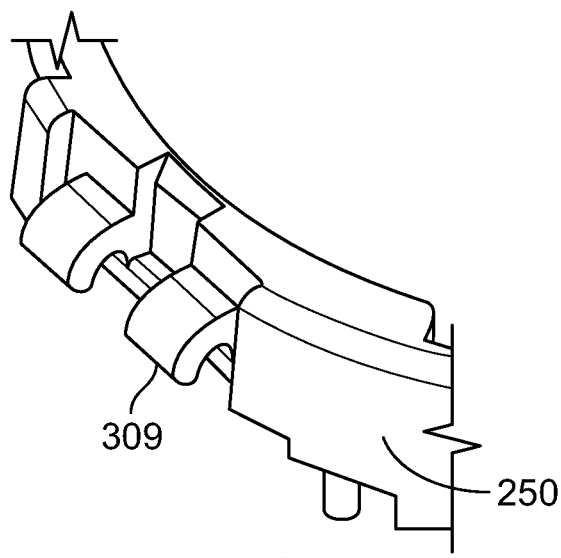
FIG. 29 is an enlarged perspective view of open hinge tabs of the retaining ring of the transfer device of FIGS. 3A-4.

As illustrated in FIGS. 3A, 4 and 28, the retainer strap 301 includes a first end having a D-shaped fastener 303 and a second end featuring hooks 305 and a pair of opposing latching pins 307. As illustrated in FIGS. 3B, 4 and 29, the retention ring 250 is provided with a pair of open hinge tabs 309. As illustrated in FIG. 3A, the hinge tabs 309 engage the D-shaped fastener 303 of the retainer strap 301 when the strap is being used to secure an injection device to the transfer device. As will be explained in greater detail below, the other end of the retainer strap (that includes the hooks 305 and the latching pins 307) is secured in the manner shown in FIG. 3A with a pressure relief assembly.

Figure 30A:
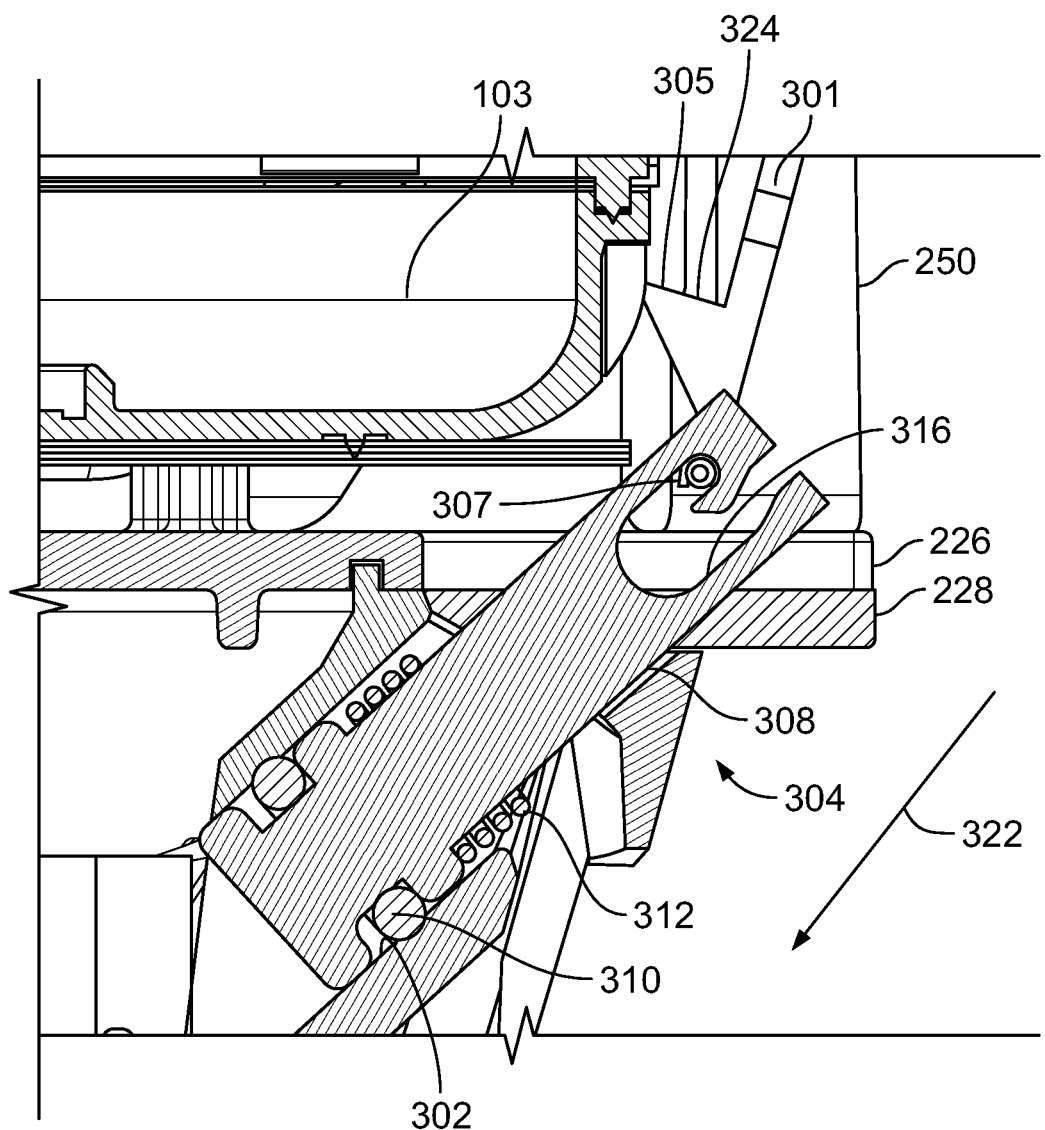
FIG. 30A is a cross-sectional view of the pressure relief assembly of the transfer device of FIGS. 3A-4 taken along a vertical cutting plane prior to use of the device and with an injection device attached.

As illustrated in FIGS. 4 and 17, the expansion chamber bottom 228 is provided with a pressure relief bore 302. As illustrated in FIGS. 30A-30D, a pressure relief assembly, indicated in general at 304, is positioned within the pressure relief bore 302. As illustrated in FIGS. 4 and 30A, the pressure relief assembly includes plunger rod 308, an O-ring 310 and a plunger rod compression spring 312. The inner end of the plunger rod 308 is provided with spaced collars 314a and 314b, between which the O-ring 310 is positioned, while the outer end of the plunger rod is provided with a J-shaped slot 316.

The transfer device 140 prior to use, and with an injection device 103 positioned thereon and secured thereto by retainer strap 301, is illustrated in FIG. 3A. The configuration of the pressure relief assembly 304 corresponding to the transfer device initial condition illustrated in FIG. 3A is illustrated in FIG. 30A. With reference to FIG. 30A, the latch pins 307 of the retainer strap 301 are engaging the closed end of the J-shaped slot 316 so as to hold the plunger rod 308 in the illustrated position against the urging of the compression spring 312, which is in the direction of arrow 322.

Furthermore, the hooks 305 of the retainer strap are hooked onto a shelf 324 on the retaining ring 250.

Figure 30B:
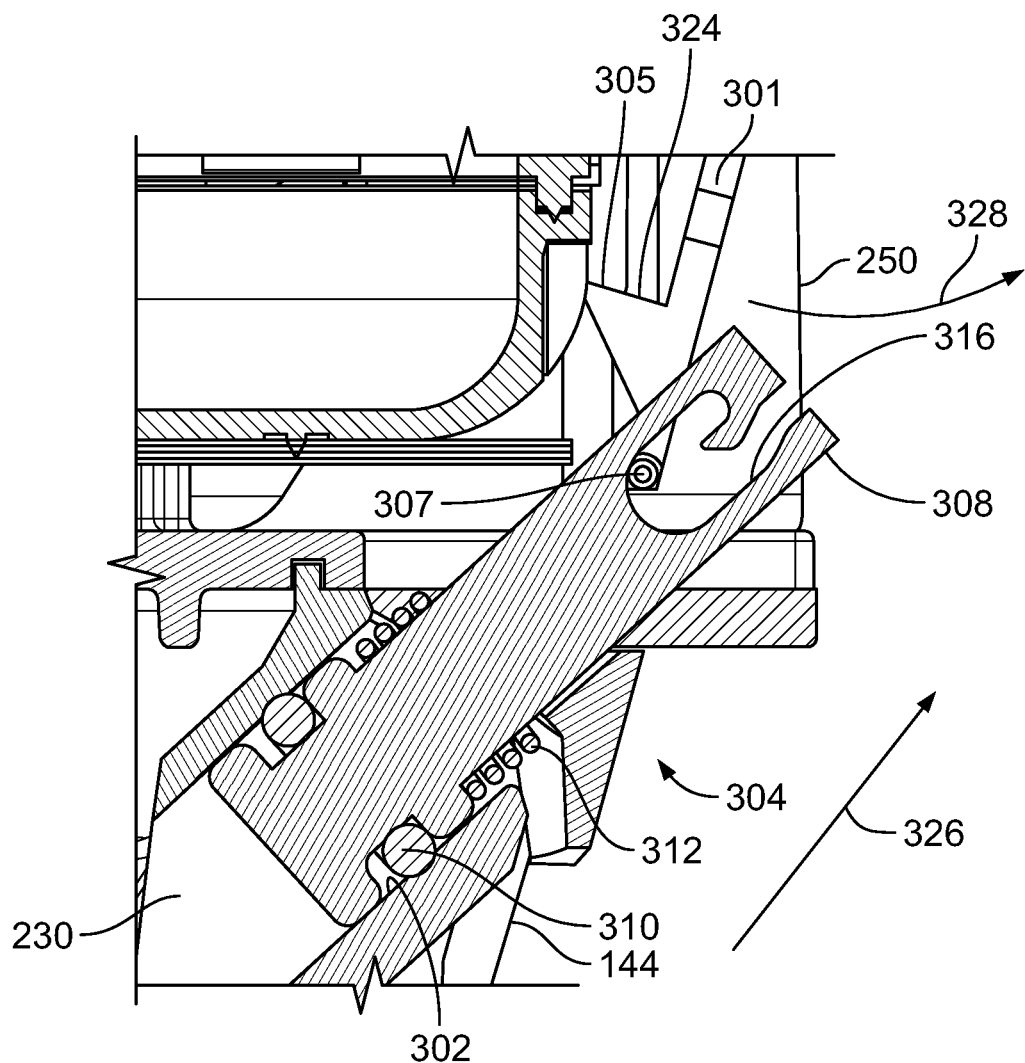
FIG. 30B is a cross-sectional view of the pressure relief assembly of the transfer device of FIGS. 3A-4 taken along a vertical cutting plane during the first portion of the fired stage.

The configuration of the pressure relieve assembly 304 during the fired stage is illustrated in FIG. 30B. The fired stage is the stage at which the user has pushed the vial into the vial elevator of the transfer device and moved it towards the retracted position so as to activate the transfer device and initiate the transfer of drug from the vial into the injection device.

As described above, the act of pushing the vial into the system causes the pressurized gas cartridge (234 of FIGS. 18 and 22) to be punctured, thus filling the internal cavity 230 of the pressurized gas expansion chamber 144 with pressurized gas. This pressure in the expansion chamber internal cavity 230 forces the plunger rod 308 in the direction of arrow 326, against the urging of the compression spring 312. The plunger rod 308 is in a closed position where the O-ring 310 reduces or eliminates leakage of the pressurized gas out of the internal cavity 230 of the expansion chamber 144. As a result, the pins 307 of the retainer strap 301 move towards the rounded bottom of the J-shaped slot 316 of the plunger rod 308, as illustrated in FIG. 30B.

Continuing with reference to FIG. 30B, the retainer strap 301 is molded (preferably from plastic) so that it has a biased, spring force inherent in the component which makes it want to swing to the right (in the direction of arrow 328). As a result, when the pins 307 are moved into the position illustrated in FIG. 30B, the hooks 305 of the retainer strap 301 move into the position on the shelf 324 of the retaining ring 250 illustrated in FIG. 30C while the pins 307 move in the J-shaped slot 316 to the position illustrated in that figure.

Figure 30C:
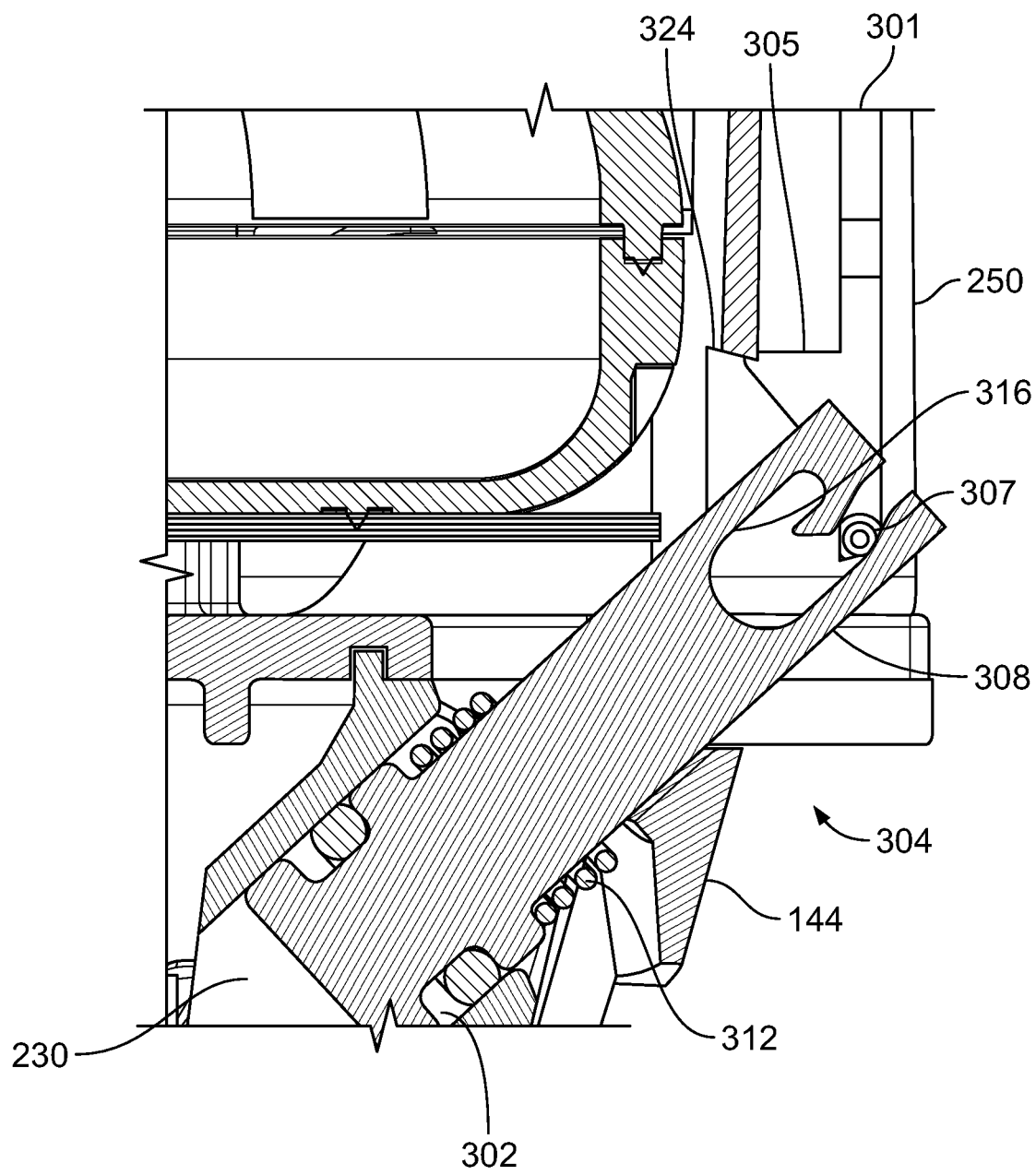
FIG. 30C is a cross-sectional view of the pressure relief assembly of the transfer device of FIGS. 3A-4 taken along a vertical cutting plane during the second portion of the fired stage.

At the time corresponding to FIG. 30C, the transfer device is transferring fluid from the vial to the injection device and there is still gas pressure inside the internal cavity 230 of the expansion chamber 144, which keeps the plunger rod 308 held in the position illustrated in FIG. 30C, again, against the urging of compression spring 312. Meanwhile, as shown in FIG. 30C, the latch pins 307 of the retainer strap 301 contact the wall of the J-shaped slot 316 of the plunger rod 308, which keeps the hooks 305 latched on the shelf 324 of the retaining ring 250.

Once the transfer of fluid is to the injection device is completed, the vent filter 293 (FIG. 27) starts to vent the compressed air in the transfer device to the atmosphere. This allows the pressure in the internal cavity 230 of the expansion chamber 144 to decrease. As the pressure in the expansion chamber 144 decreases, the compression spring 312 begins to expand or extend (extension of spring not shown) and the plunger rod 308 moves in the direction of arrow 322 of FIG. 30A into the position illustrated in FIG. 30D. As a result, the latch pins 307 of the retainer strap 301 exit the open end of the J-shaped slot 316 of the plunger rod 308 so that the hooks 305 of the retainer strap 301 (due to the molded bias of the retainer strap) disengage the shelf 324 of the retainer ring 250, and the end of the retainer strap is released, as illustrated in FIG. 30D.

The characteristics of the compression spring 312 can be selected to retract at a specific pressure of the internal cavity 230 of the expansion chamber 144, thus allowing the retainer strap 301 to be unlocked at a specific pressure.

Figure 30D:
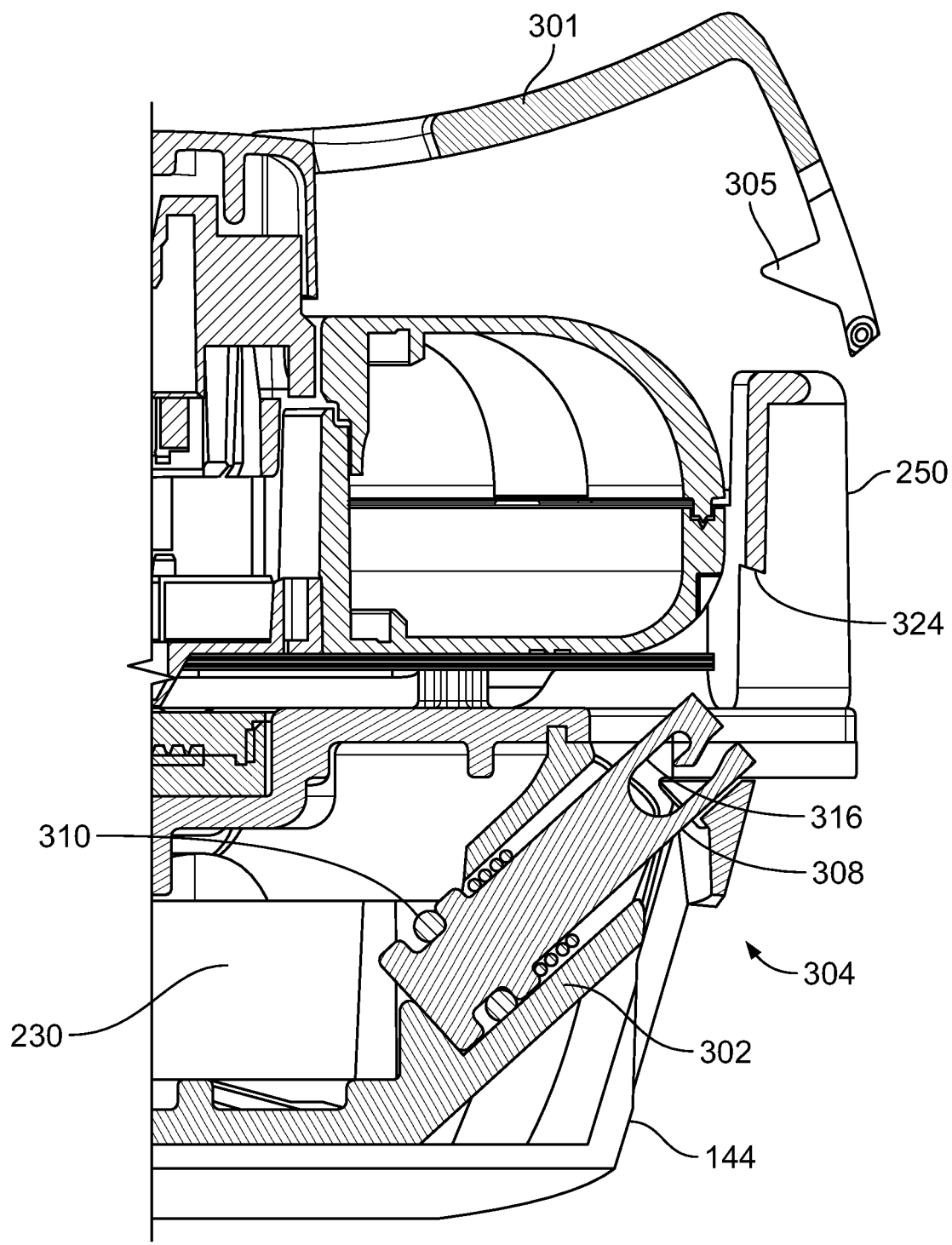
FIG. 30D is a cross-sectional view of the pressure relief assembly of the transfer device of FIGS. 3A-4 taken along a vertical cutting plane during a final venting stage.

With continued reference to FIG. 30D, the plunger rod 308 also acts as a final air vent to release any additional pressure in the expansion chamber 144. This occurs once the O-ring 310 passes the "vent position" (illustrated in FIG. 30D) in the pressure relief bore 302 when the plunger rod 308 is in the vent position, thus allowing the remaining pressurized air to escape the internal cavity 230 of the expansion chamber 144 past the O-ring and plunger rod.

Figure 31:
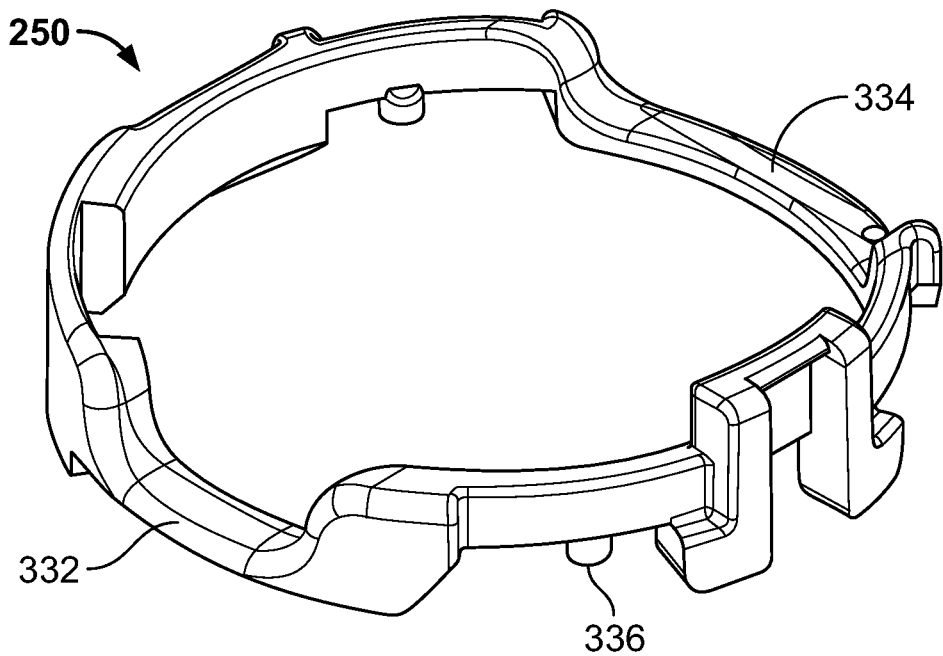
FIG. 31 is an enlarged perspective view of the retaining ring of the transfer device of FIGS. 3A-4.

With reference to FIG. 31, where the retaining ring is illustrated as removed from the transfer device and indicated in general at 250, a front finger cutout is indicated at 332 and a rear finger cutout is indicated at 334. The front finger cutout 332 allows for the thumb placement for removal of the injection device when attached to the transfer device (as illustrated in FIG. 3A), while the rear finger cutout 334 allows for multiple finger placement for removal of the injection device when attached to the transfer device.

Figure 32:
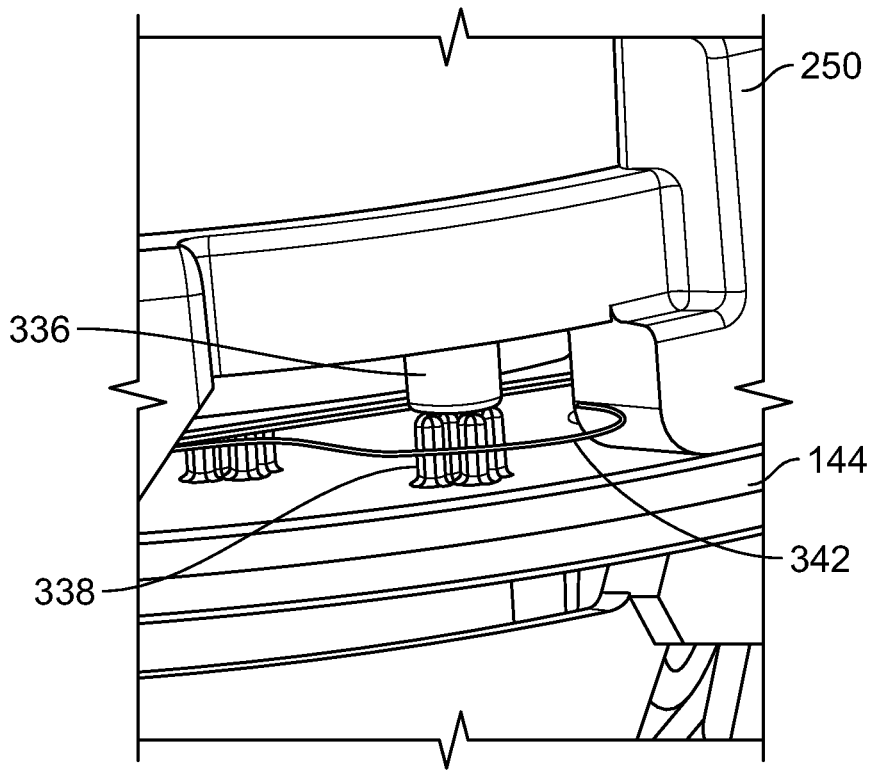
FIG. 32 is an enlarged view of a portion of the retaining ring of FIG. 31 showing cooperating posts for retaining the an injection device adhesive liner tab or safety strip.

Furthermore, with reference to FIGS. 31 and 32, the retaining ring includes downwardly extending adhesive capture posts 336 that cooperate with corresponding posts 338 formed on the top of the expansion chamber 144 to mechanically capture the adhesive tabs 342 of a release liner. The release liner removably covers the adhesive covered surface of the injection device which is used to secure the injection device to a user. As a result, the release liner remains with the transfer device when the injection device is being pulled out of the retaining ring 250 of the transfer device. In addition, the cooperating posts 336 and 338 may be used to capture the distal end of a safety strip that is attached to the injection device to prevent accidental activation of the injection device. The posts 336 and 338 retain the distal end of the safety strip so that the safety strip is automatically removed from the injection device when it is pulled from the retaining ring 250 of the transfer device, and the injection device is thus ready to activate to perform the injection.

The retaining ring 250 therefore makes assembly of the injection device to the transfer device easier. Instead of having to tuck the injection device safety strip and release liner adhesive tabs somehow into the transfer device, attachment of the retaining ring 250 to the expansion chamber 144 is the final step in assembly and captures the safety strip and tabs and thus mechanically locks to the adhesive liner and safety strip.

Although the present subject matter is described herein with reference to specific structures, methods and examples, this is for purposes of illustration only, and it is understood that the present subject matter is applicable to a large range of devices and systems that may differ in particular configuration and appearance while still employing this subject matter.

What is claimed is:
1. A transfer device for transferring a medical fluid from a vial to a medical fluid injection device comprising:
   a) a vial holder;
   b) a vial spike positioned within the vial holder and configured so that the vial spike enters a vial positioned within the vial holder;

c) an injection device support surface connected to the vial holder;
d) a liquid outlet port mounted to or within the injection device support surface, said liquid outlet port in fluid communication with the vial spike;
e) a retaining ring mounted to the injection device support surface and configured to at least partially surround an injection device positioned on the injection device support surface;
f) wherein the retaining ring includes a first retaining ring adhesive capture post connected to a portion of the retaining ring that is spaced from the injection device support surface, wherein said first retaining ring adhesive, capture post extends from the portion of the retaining ring towards the injection device support surface and is configured to engage a release liner that removably covers an adhesive covered surface of the injection device when the injection device is mounted to the injection device support surface.

2. The transfer device of claim 1 wherein the retaining ring includes a front finger cutout and a rear finger cutout, wherein the front finger cutout is configured to allow for thumb placement on an injection device for removal of the injection device when it is attached to the transfer device and the rear finger cutout is configured to allow for multiple finger placement on the injection device for removal of the injection device when it is attached to the transfer device.

3. The transfer device of claim 1 further comprising a first cooperating post mounted to the injection device support surface, said first cooperating post configured to cooperate with the first retaining ring adhesive capture post to engage the release liner that removably covers the adhesive covered surface of the injection device when the injection device is mounted to the injection device support surface.

4. The transfer device of claim 1 comprising a second retaining ring adhesive capture post connected to a portion of the retaining ring that is spaced from the injection device support surface, wherein said second retaining ring adhesive capture post extends from the portion of the retaining ring towards the injection device support surface and is configured to engage the release liner that removably covers the adhesive covered surface of the injection device when the injection device is mounted to the injection device support surface.

5. The transfer device of claim 4 further comprising a first cooperating post and a second cooperating post mounted to the injection device support surface, said first cooperating post configured to cooperate with the first retaining ring adhesive capture post and said second cooperating post configured to cooperate with the second retaining ring adhesive capture post to engage the release liner that removably covers the adhesive covered surface of the injection device when the injection device is mounted to the injection device support surface.

6. The transfer device of claim 1 further comprising a retainer strap configured to secure an injection device to the injection device support surface of the transfer device, said retainer strap having a pivot end and a hook end, where both the pivot end and the hood end are attached to the transfer device.

7. The transfer device of claim 6 wherein the pivot end of the retainer strap is attached to the retaining ring.

8. The transfer device of claim 1 further comprising:
g) an expansion chamber having an interior cavity and an expansion chamber top, wherein the expansion chamber top defines the injection device support surface;
h) a pressurized gas cartridge positioned with the interior cavity of the expansion chamber;
i) a puncture tip configured to puncture the pressurized gas cartridge when actuated by a user;
j) said vial spike in fluid communication with the interior cavity of the expansion chamber.

9. The transfer device of claim 8 wherein the vial spike includes a liquid inlet that is in fluid communication with the liquid outlet port of the transfer device and a gas outlet opening that is in fluid communication with the interior cavity of the expansion chamber, said gas outlet opening positioned above the liquid inlet of the vial spike when the vial spike is in a vial.

10. The transfer device of claim 1 wherein the retaining ring is mounted to a periphery of the injection device support surface.

11. The transfer device of claim 10 wherein the injection device support surface is generally circular.

12. The transfer device of claim 10 wherein the retaining ring includes a front finger cutout and a rear finger cutout, wherein the front finger cutout is configured to allow for thumb placement on an injection device for removal of the injection device when it is attached to the transfer device and the rear finger cutout is configured to allow for multiple finger placement on the injection device for removal of the injection device when it is attached to the transfer device.

13. A transfer device for transferring a medical fluid from a vial to a medical fluid injection device comprising:
a) a vial holder;
b) a vial spike positioned within the vial holder and configured so that the vial spike enters a vial positioned within the vial holder;
c) an injection device support surface connected to the vial holder;
d) a liquid outlet port mounted to or within the injection device support surface, said liquid outlet port in fluid communication with the vial spike;
e) a retaining ring mounted to the injection device support surface and configured to at least partially surround an injection device positioned on the injection device support surface;
f) an injection device mounted to the injection device support surface;
g) a retainer strap securing the injection device to the injection device support surface of the transfer device, said retainer strap having a pivot end and a hook end, where both the pivot end and the hood end are attached to the transfer device.

14. The transfer device of claim 13 wherein the pivot end of the retainer strap is attached to the retaining ring.

15. The transfer device of claim 13 wherein the retaining ring is mounted to a periphery of the injection device support surface.

16. The transfer device of claim 15 wherein the retaining ring includes a front finger cutout and a rear finger cutout, wherein the front finger cutout is configured to allow for thumb placement on an injection device for removal of the injection device when it is attached to the transfer device and the rear finger cutout is configured to allow for multiple finger placement on the injection device for removal of the injection device when it is attached to the transfer device.

17. The transfer device of claim 13 wherein the retainer ring includes a pair of hinge tabs that receive the pivot end of the retainer strap.

18. The transfer device of claim 17 wherein the pair of hinge tabs are open hinge tabs.

19. The transfer device of claim 17 wherein the pivot end of the retainer strap includes a D-shaped fastener that is received by the pair of hinge tabs.

20. The transfer device of claim 19 wherein the pair of hinge tabs are open hinge tabs.

* * * * *